US012667674B2

(12) United States Patent (10) Patent No.: US 12,667,674 B2

Helgeson (45) Date of Patent: Jun. 30, 2026

(54) INJECTION SITE DETERMINATION SYSTEMS AND METHODS FOR INJECTION SITE TRACKING AND RECOMMENDING INJECTION SITES

(71) Applicant: Bigfoot Biomedical, Inc., Milpitas, CA (US)

(72) Inventor: Stuart Helgeson, San Francisco, CA (US)

(73) Assignee: BIGFOOT BIOMEDICAL, INC., Milpitas, CA (US)

( * ) Notice: Subject to any disclaimer, the term of this patent is extended or adjusted under 35 U.S.C. 154(b) by 1195 days.

(21) Appl. No.: 17/449,157

(22) Filed: Sep. 28, 2021

(65) Prior Publication Data

US 2022/0105282 A1 Apr. 7, 2022

Related U.S. Application Data

(60) Provisional application No. 63/086,847, filed on Oct. 2, 2020.

(51) Int. Cl.
G16H 20/17 (2018.01)
A61M 5/42 (2006.01)
(Continued)

(52) U.S. Cl.
CPC ............ A61M 5/427 (2013.01); G16H 20/17 (2018.01); G16H 40/67 (2018.01); G16H 50/20 (2018.01);
(Continued)

(58) Field of Classification Search
CPC .......... A61M 5/427; A61M 2005/3125; A61M 2230/201; G16H 20/17; G16H 50/20; G16H 40/67; G16H 50/70
See application file for complete search history.

(56) References Cited

U.S. PATENT DOCUMENTS 4,498,904 A 2/1985 Turner et al.
4,515,584 A 5/1985 Abe et al.
(Continued)

FOREIGN PATENT DOCUMENTS

CA 2925458 A1 4/2015
CN 201248860 Y 6/2009
(Continued)

OTHER PUBLICATIONS

"Calculating Insulin Dose." Diabetes Education Online, University of California, San Francisco, https://web.archive.org/web/20110711172015/dtc.ucsf.edu/types-of-diabetes/type2/treatment-of-type-2-diabetes/medications-and-therapies/type-2-insulin-rx/calculating-insulin-dose/. Retrieved Feb. 2021. (Year: 2011).
(Continued)

*Primary Examiner* — Bhisma Mehta
*Assistant Examiner* — Haden Matthew Ritchie
(74) *Attorney, Agent, or Firm* — HSML P.C.

(57) ABSTRACT

A method of improving insulin delivery includes detecting a dosing event of an upcoming insulin dose, identifying a next injection site to recommend to a user for the upcoming insulin dose, and transmitting a recommended injection site to a delivery device to be displayed on the delivery device. The method further includes receiving a user selection of a plurality of injection sites to include within an injection site recommendation profile, receiving a user selection of an injection cycle to utilize within the injection site recommendation profile, and generating an injection site recommendation profile.

18 Claims, 15 Drawing Sheets

(51) Int. Cl.

| | |
|---|---|
| *G16H 40/67* | (2018.01) |
| *G16H 50/20* | (2018.01) |
| *G16H 50/70* | (2018.01) |
| *A61M 5/31* | (2006.01) |

(52) U.S. Cl.
CPC ..... *G16H 50/70* (2018.01); *A61M 2005/3125* (2013.01); *A61M 2205/14* (2013.01); *A61M 2230/201* (2013.01)

(56) References Cited

U.S. PATENT DOCUMENTS

| | | | |
|---|---|---|---|
| 4,950,216 A | 8/1990 | Weder |
| 4,973,318 A | 11/1990 | Holm et al. |
| 4,988,660 A | 1/1991 | Campbell |
| 5,233,571 A | 8/1993 | Wirtschafter |
| 5,279,586 A | 1/1994 | Balkwill |
| 5,523,560 A | 6/1996 | Manique et al. |
| 5,536,249 A | 7/1996 | Castellano et al. |
| 5,564,414 A | 10/1996 | Walker et al. |
| 5,626,566 A | 5/1997 | Petersen et al. |
| 5,640,954 A | 6/1997 | Pfeiffer et al. |
| 5,645,534 A | 7/1997 | Chanoch |
| 5,665,065 A | 9/1997 | Colman et al. |
| 5,678,571 A | 10/1997 | Brown |
| 5,681,285 A | 10/1997 | Ford et al. |
| 5,822,715 A | 10/1998 | Worthington et al. |
| 5,918,603 A | 7/1999 | Brown |
| 5,925,021 A | 7/1999 | Castellano et al. |
| 5,984,900 A | 11/1999 | Mikkelsen |
| 6,004,297 A | 12/1999 | Steenfeldt-Jensen et al. |
| 6,032,119 A | 2/2000 | Brown et al. |
| 6,042,571 A | 3/2000 | Hjertman et al. |
| 6,235,004 B1 | 5/2001 | Steenfeldt-Jensen et al. |
| 6,287,283 B1 | 9/2001 | Ljunggreen et al. |
| 6,302,855 B1 | 10/2001 | Lav et al. |
| 6,354,996 B1 | 3/2002 | Drinan et al. |
| 6,482,185 B1 | 11/2002 | Hartmann |
| 6,650,951 B1 | 11/2003 | Jones et al. |
| 6,685,678 B2 | 2/2004 | Evans et al. |
| 6,810,290 B2 | 10/2004 | Lebel et al. |
| 6,817,986 B2 | 11/2004 | Slate et al. |
| 6,827,702 B2 | 12/2004 | Lebel et al. |
| 6,956,572 B2 | 10/2005 | Zaleski |
| 7,025,743 B2 | 4/2006 | Mann et al. |
| 7,109,878 B2 | 9/2006 | Mann et al. |
| 7,133,329 B2 | 11/2006 | Skyggebjerg et al. |
| 7,241,265 B2 | 7/2007 | Cummings et al. |
| 7,291,107 B2 | 11/2007 | Hellwig et al. |
| 7,343,197 B2 | 3/2008 | Shusterman |
| 7,397,730 B2 | 7/2008 | Skyggebjerg et al. |
| 7,404,796 B2 | 7/2008 | Ginsberg |
| 7,454,359 B2 | 11/2008 | Rosenfeld et al. |
| 7,553,281 B2 | 6/2009 | Hellwig et al. |
| 7,570,980 B2 | 8/2009 | Ginsberg |
| 7,591,801 B2 | 9/2009 | Brauker et al. |
| 7,647,237 B2 | 1/2010 | Malave et al. |
| 7,713,229 B2 | 5/2010 | Veit et al. |
| 7,751,907 B2 | 7/2010 | Blomquist |
| 7,837,647 B2 | 11/2010 | Estes et al. |
| 7,850,641 B2 | 12/2010 | Lebel et al. |
| 7,871,376 B2 | 1/2011 | Brown |
| 7,878,975 B2 | 2/2011 | Liljeryd et al. |
| 7,905,833 B2 | 3/2011 | Brister et al. |
| 7,931,613 B2 | 4/2011 | Haueter et al. |
| 7,955,303 B2 | 6/2011 | Burren et al. |
| 7,976,492 B2 | 7/2011 | Brauker et al. |
| 8,012,119 B2 | 9/2011 | Estes et al. |
| 8,052,655 B2 | 11/2011 | Moeller et al. |
| 8,108,299 B1 | 1/2012 | Waelbroeck et al. |
| 8,127,946 B2 | 3/2012 | Winig et al. |
| 8,132,101 B2 | 3/2012 | Buck et al. |
| 8,156,070 B2 | 4/2012 | Buck et al. |
| 8,206,340 B2 | 6/2012 | Arefieg |
| 8,217,946 B2 | 7/2012 | Halpern et al. |
| 8,219,222 B2 | 7/2012 | Blomquist |
| 8,221,345 B2 | 7/2012 | Blomquist |
| 8,221,356 B2 | 7/2012 | Enggaard et al. |
| 8,229,535 B2 | 7/2012 | Mensinger et al. |
| 8,231,531 B2 | 7/2012 | Brister et al. |
| 8,231,562 B2 | 7/2012 | Buck et al. |
| 8,237,715 B2 | 8/2012 | Buck et al. |
| 8,250,483 B2 | 8/2012 | Blomquist |
| D667,948 S | 9/2012 | Moldenhauer |
| 8,257,652 B2 | 9/2012 | Drucker et al. |
| 8,257,653 B2 | 9/2012 | Drucker et al. |
| 8,266,906 B2 | 9/2012 | Wu et al. |
| 8,273,296 B2 | 9/2012 | Drucker et al. |
| 8,279,226 B2 | 10/2012 | Krieftewirth |
| RE43,834 E | 11/2012 | Steenfeldt-Jensen et al. |
| 8,310,415 B2 | 11/2012 | Mclaughlin et al. |
| 8,333,752 B2 | 12/2012 | Veit et al. |
| 8,337,469 B2 | 12/2012 | Eberhart et al. |
| 8,357,091 B2 | 1/2013 | Say et al. |
| 8,365,065 B2 | 1/2013 | Gejdos et al. |
| 8,372,005 B2 | 2/2013 | Say et al. |
| 8,439,834 B2 | 5/2013 | Schmelzeisen-Redeker et al. |
| 8,444,595 B2 | 5/2013 | Brukalo et al. |
| 8,460,231 B2 | 6/2013 | Brauker et al. |
| 8,514,086 B2 | 8/2013 | Harper et al. |
| 8,529,838 B2 | 9/2013 | Drucker et al. |
| 8,529,839 B2 | 9/2013 | Drucker et al. |
| 8,529,841 B2 | 9/2013 | Drucker et al. |
| 8,551,039 B2 | 10/2013 | Veit et al. |
| 8,556,865 B2 | 10/2013 | Krulevitch et al. |
| 8,556,867 B2 | 10/2013 | Krulevitch et al. |
| 8,562,558 B2 | 10/2013 | Kamath et al. |
| 8,565,848 B2 | 10/2013 | Brister et al. |
| D694,252 S | 11/2013 | Helm |
| 8,579,815 B2 | 11/2013 | Galley et al. |
| 8,591,455 B2 | 11/2013 | Mensinger et al. |
| 8,601,005 B2 | 12/2013 | Bousamra et al. |
| 8,615,366 B2 | 12/2013 | Galley et al. |
| 8,622,906 B2 | 1/2014 | Say et al. |
| 8,657,779 B2 | 2/2014 | Blomquist |
| 8,663,109 B2 | 3/2014 | Brister et al. |
| 8,719,945 B2 | 5/2014 | Birtwhistle et al. |
| 8,721,585 B2 | 5/2014 | Brauker et al. |
| 8,738,925 B1 | 5/2014 | Park et al. |
| 8,743,662 B2 | 6/2014 | Sjolund et al. |
| 8,750,955 B2 | 6/2014 | Brister et al. |
| 8,756,074 B2 | 6/2014 | Brzustowicz |
| 8,761,940 B2 | 6/2014 | Long et al. |
| 8,774,887 B2 | 7/2014 | Say et al. |
| 8,808,228 B2 | 8/2014 | Brister et al. |
| 8,816,862 B2 | 8/2014 | Harper et al. |
| 8,817,258 B2 | 8/2014 | Whalley et al. |
| 8,821,452 B2 | 9/2014 | Dasbach et al. |
| 8,882,722 B2 | 11/2014 | Bode et al. |
| 8,882,741 B2 | 11/2014 | Brauker et al. |
| 8,895,315 B2 | 11/2014 | Batman et al. |
| 8,920,401 B2 | 12/2014 | Brauker et al. |
| 8,926,585 B2 | 1/2015 | Brauker et al. |
| 8,932,250 B2 | 1/2015 | Montgomery et al. |
| 8,961,465 B2 | 2/2015 | Blomquist |
| 8,992,464 B2 | 3/2015 | Bashan et al. |
| D727,928 S | 4/2015 | Allison et al. |
| 9,008,803 B2 | 4/2015 | Blomquist |
| 9,020,572 B2 | 4/2015 | Mensinger et al. |
| 9,022,996 B2 | 5/2015 | Eberhart et al. |
| 9,033,877 B2 | 5/2015 | Werner et al. |
| 9,041,730 B2 | 5/2015 | Johnson et al. |
| 9,050,409 B2 | 6/2015 | Haueter et al. |
| 9,050,413 B2 | 6/2015 | Brauker et al. |
| 9,072,477 B2 | 7/2015 | Say et al. |
| 9,089,650 B2 | 7/2015 | Nielsen et al. |
| 9,101,723 B2 | 8/2015 | Larsen |
| 9,108,006 B2 | 8/2015 | Jensen et al. |
| D738,385 S | 9/2015 | Lim et al. |
| 9,125,991 B2 | 9/2015 | Schabbach et al. |
| 9,134,823 B2 | 9/2015 | Grant et al. |
| 9,136,939 B2 | 9/2015 | Galley et al. |
| 9,143,569 B2 | 9/2015 | Mensinger et al. |
| 9,155,843 B2 | 10/2015 | Brauker et al. |

(56)  References Cited

U.S. PATENT DOCUMENTS

| | | | |
|---|---|---|---|
| 9,159,148 B2 | 10/2015 | Boyer et al. |
| 9,186,113 B2 | 11/2015 | Harper et al. |
| 9,198,623 B2 | 12/2015 | Fern et al. |
| D747,333 S | 1/2016 | Supino et al. |
| D748,101 S | 1/2016 | Bang et al. |
| D748,126 S | 1/2016 | Sarukkai et al. |
| 9,233,210 B2 | 1/2016 | Bock et al. |
| D749,103 S | 2/2016 | Song |
| 9,250,111 B2 | 2/2016 | Whalley et al. |
| 9,255,830 B2 | 2/2016 | Whalley et al. |
| D753,685 S | 4/2016 | Zimmerman et al. |
| D754,689 S | 4/2016 | Lee |
| D759,684 S | 6/2016 | Bijlani et al. |
| 9,358,334 B2 | 6/2016 | Arefieg |
| D761,280 S | 7/2016 | Chung et al. |
| D763,308 S | 8/2016 | Wang et al. |
| D766,958 S | 9/2016 | Salazar et al. |
| 9,435,666 B2 | 9/2016 | Richter |
| 9,446,194 B2 | 9/2016 | Kamath et al. |
| 9,483,620 B2 | 11/2016 | Reimer |
| 9,498,155 B2 | 11/2016 | Brauker et al. |
| 9,501,219 B2 | 11/2016 | Yoshimoto et al. |
| 9,526,838 B2 | 12/2016 | Baran et al. |
| D777,760 S | 1/2017 | Zhao et al. |
| 9,545,482 B2 | 1/2017 | Binier |
| 9,561,324 B2 | 2/2017 | Estes |
| D781,890 S | 3/2017 | Gathman et al. |
| 9,604,004 B2 | 3/2017 | Jakobsen |
| D783,037 S | 4/2017 | Hariharan et al. |
| D783,648 S | 4/2017 | Vazquez et al. |
| D784,391 S | 4/2017 | Yuguchi et al. |
| D785,025 S | 4/2017 | Zimmerman et al. |
| 9,619,625 B2 | 4/2017 | Bengtsson |
| 9,623,188 B2 | 4/2017 | Nielsen et al. |
| 9,629,901 B2 | 4/2017 | Estes |
| D786,273 S | 5/2017 | Herman et al. |
| 9,636,461 B2 | 5/2017 | Bengtsson et al. |
| 9,636,464 B1 | 5/2017 | Binier |
| 9,638,564 B2 | 5/2017 | Whalley et al. |
| 9,642,968 B2 | 5/2017 | Whalley et al. |
| 9,649,448 B2 | 5/2017 | Madsen |
| 9,651,482 B2 | 5/2017 | Blei et al. |
| 9,672,328 B2 | 6/2017 | Saint et al. |
| 9,675,761 B2 | 6/2017 | Hoeholt et al. |
| D791,806 S | 7/2017 | Brewington et al. |
| D794,047 S | 8/2017 | Gandhi et al. |
| D795,900 S | 8/2017 | Bischoff et al. |
| D795,919 S | 8/2017 | Bischoff et al. |
| D795,927 S | 8/2017 | Bischoff et al. |
| 9,721,176 B2 | 8/2017 | Prager |
| 9,730,621 B2 | 8/2017 | Cohen et al. |
| 9,734,302 B2 | 8/2017 | Nielsen et al. |
| 9,737,665 B2 | 8/2017 | Heumann et al. |
| D797,760 S | 9/2017 | Tsujimura et al. |
| D798,312 S | 9/2017 | Tsujimura et al. |
| 9,750,882 B2 | 9/2017 | Blei et al. |
| 9,750,886 B2 | 9/2017 | Plambech et al. |
| 9,775,543 B2 | 10/2017 | Brister et al. |
| 9,782,543 B2 | 10/2017 | Groeschke et al. |
| 9,782,544 B2 | 10/2017 | Heumann et al. |
| 9,788,172 B1 | 10/2017 | Ewe et al. |
| 9,789,260 B1 | 10/2017 | Binier |
| 9,790,977 B2 | 10/2017 | Baran et al. |
| D802,760 S | 11/2017 | Neby |
| 9,833,576 B2 | 12/2017 | Windum et al. |
| 9,848,774 B2 | 12/2017 | Bergstrom et al. |
| D808,986 S | 1/2018 | Dudey |
| D809,544 S | 2/2018 | Ambielli |
| D809,545 S | 2/2018 | Ban et al. |
| D811,425 S | 2/2018 | Olsen et al. |
| D815,127 S | 4/2018 | Phillips et al. |
| D815,667 S | 4/2018 | Yeung |
| D819,043 S | 5/2018 | Yamaura et al. |
| 9,980,140 B1 | 5/2018 | Spencer et al. |
| D820,297 S | 6/2018 | Gardner et al. |
| 9,996,668 B2 | 6/2018 | Reihman et al. |
| 10,016,565 B2 | 7/2018 | Nielsen et al. |
| 10,043,093 B2 | 8/2018 | Allerdings et al. |
| 10,071,205 B2 | 9/2018 | Blei et al. |
| D831,049 S | 10/2018 | Agarwal et al. |
| D831,684 S | 10/2018 | Ghosh |
| D832,292 S | 10/2018 | Hu et al. |
| 10,086,141 B2 | 10/2018 | Steel et al. |
| 10,105,094 B2 | 10/2018 | Baran et al. |
| 10,105,497 B2 | 10/2018 | Dreier et al. |
| D832,870 S | 11/2018 | Hu |
| D833,469 S | 11/2018 | Coleman et al. |
| D834,710 S | 11/2018 | Michael |
| 10,117,996 B2 | 11/2018 | Stefansen |
| 10,117,999 B2 | 11/2018 | Andersen |
| 10,133,948 B2 | 11/2018 | Hammen |
| D835,118 S | 12/2018 | Lee et al. |
| 10,155,090 B2 | 12/2018 | Larsen et al. |
| 10,159,797 B2 | 12/2018 | Andersen et al. |
| 10,159,798 B2 | 12/2018 | Blei et al. |
| D837,807 S | 1/2019 | Baber et al. |
| D838,734 S | 1/2019 | Kruse et al. |
| 10,166,338 B2 | 1/2019 | Nielsen et al. |
| 10,166,340 B2 | 1/2019 | Blei et al. |
| 10,169,539 B2 | 1/2019 | Reihman et al. |
| 10,173,015 B2 | 1/2019 | Fiedler et al. |
| 10,179,207 B2 | 1/2019 | Haupt |
| 10,183,119 B2 | 1/2019 | Andersen et al. |
| 10,183,120 B2 | 1/2019 | Sihlanick et al. |
| 10,190,901 B2 | 1/2019 | Whalley et al. |
| 10,195,351 B2 | 2/2019 | Allerdings et al. |
| 10,195,352 B2 | 2/2019 | Baran et al. |
| 10,195,355 B2 | 2/2019 | Allerdings et al. |
| D842,888 S | 3/2019 | Krainer et al. |
| D843,402 S | 3/2019 | Casse et al. |
| D846,590 S | 4/2019 | Cabrera et al. |
| D847,165 S | 4/2019 | Kolbenheyer |
| D849,757 S | 5/2019 | Jing et al. |
| 10,296,128 B1 | 5/2019 | Nold et al. |
| 10,341,866 B1 | 7/2019 | Spencer et al. |
| 10,524,110 B1 | 12/2019 | Klem et al. |
| 10,667,759 B2 | 6/2020 | Duke et al. |
| 10,686,898 B1 | 6/2020 | Phillips et al. |
| 10,702,658 B2 | 7/2020 | Shekalim |
| 10,896,245 B2 | 1/2021 | Crothall et al. |
| 2003/0028089 A1 | 2/2003 | Galley et al. |
| 2003/0032868 A1 | 2/2003 | Graskov et al. |
| 2003/0065536 A1 | 4/2003 | Hansen et al. |
| 2004/0039255 A1 | 2/2004 | Simonsen et al. |
| 2004/0062148 A1 | 4/2004 | Skyggebjerg et al. |
| 2004/0093331 A1 | 5/2004 | Garner et al. |
| 2004/0153257 A1 | 8/2004 | Munk |
| 2005/0005121 A1 | 1/2005 | Chen et al. |
| 2005/0038674 A1 | 2/2005 | Braig et al. |
| 2005/0049179 A1 | 3/2005 | Davidson et al. |
| 2005/0192557 A1 | 9/2005 | Brauker et al. |
| 2006/0036144 A1 | 2/2006 | Brister et al. |
| 2006/0173417 A1 | 8/2006 | Rosen et al. |
| 2007/0021715 A1 | 1/2007 | Kohlbrenner et al. |
| 2007/0173708 A9 | 7/2007 | Dobbles et al. |
| 2007/0186923 A1 | 8/2007 | Poutiatine et al. |
| 2007/0239486 A1 | 10/2007 | Gordon |
| 2008/0119705 A1 | 5/2008 | Patel et al. |
| 2008/0162192 A1 | 7/2008 | Vonk et al. |
| 2008/0188813 A1 | 8/2008 | Miller et al. |
| 2008/0201169 A1 | 8/2008 | Galasso et al. |
| 2008/0228057 A1 | 9/2008 | Graskov et al. |
| 2008/0234663 A1 | 9/2008 | Yodfat et al. |
| 2008/0235053 A1 | 9/2008 | Ray et al. |
| 2008/0262469 A1 | 10/2008 | Brister et al. |
| 2008/0287755 A1 | 11/2008 | Sass et al. |
| 2008/0300572 A1 | 12/2008 | Rankers et al. |
| 2008/0310676 A1 | 12/2008 | Silver |
| 2008/0312512 A1 | 12/2008 | Brukalo et al. |
| 2008/0312584 A1 | 12/2008 | Montgomery et al. |
| 2009/0036771 A1 | 2/2009 | Fago et al. |
| 2009/0048561 A1 | 2/2009 | Burren et al. |
| 2009/0103124 A1 | 4/2009 | Kimura et al. |
| 2009/0120716 A1 | 5/2009 | Yamamoto et al. |

(56) References Cited

U.S. PATENT DOCUMENTS

| | | |
|---|---|---|
| 2009/0131875 A1 | 5/2009 | Green |
| 2009/0144089 A1 | 6/2009 | Heywood et al. |
| 2009/0163793 A1 | 6/2009 | Koehler et al. |
| 2009/0171589 A1 | 7/2009 | Kovatchev |
| 2009/0177154 A1 | 7/2009 | Blomquist |
| 2009/0209938 A1 | 8/2009 | Matti |
| 2009/0240440 A1 | 9/2009 | Shurabura et al. |
| 2009/0299276 A1 | 12/2009 | Brauker et al. |
| 2009/0299279 A1 | 12/2009 | Richter |
| 2009/0318865 A1 | 12/2009 | Moeller et al. |
| 2010/0017141 A1 | 1/2010 | Campbell et al. |
| 2010/0049126 A1 | 2/2010 | Bronfeld et al. |
| 2010/0058060 A1 | 3/2010 | Schneider |
| 2010/0063438 A1 | 3/2010 | Bengtsson |
| 2010/0081993 A1 | 4/2010 | O'Connor |
| 2010/0095229 A1 | 4/2010 | Dixon et al. |
| 2010/0198520 A1 | 8/2010 | Breton et al. |
| 2010/0292634 A1 | 11/2010 | Kircher et al. |
| 2010/0305965 A1 | 12/2010 | Benjamin et al. |
| 2010/0331656 A1 | 12/2010 | Mensinger et al. |
| 2011/0009727 A1 | 1/2011 | Mensinger et al. |
| 2011/0124996 A1 | 5/2011 | Reinke et al. |
| 2011/0178462 A1 | 7/2011 | Moberg et al. |
| 2011/0184343 A1 | 7/2011 | Veit et al. |
| 2011/0191343 A1 | 8/2011 | Heaton et al. |
| 2011/0201911 A1 | 8/2011 | Johnson et al. |
| 2011/0270158 A1 | 11/2011 | Brauker et al. |
| 2011/0275986 A1 | 11/2011 | Bashan et al. |
| 2011/0281791 A1 | 11/2011 | Zion et al. |
| 2011/0282409 A1 | 11/2011 | Ternes et al. |
| 2011/0295215 A1 | 12/2011 | Nielsen et al. |
| 2011/0313350 A1 | 12/2011 | Krulevitch et al. |
| 2011/0313395 A1 | 12/2011 | Krulevitch et al. |
| 2012/0046606 A1 | 2/2012 | Arefieg |
| 2012/0072236 A1 | 3/2012 | Atkin |
| 2012/0078665 A1 | 3/2012 | Johnson et al. |
| 2012/0165746 A1 | 6/2012 | Harms et al. |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0238852 A1 | 9/2012 | Brauker et al. |
| 2012/0238853 A1 | 9/2012 | Arefieg |
| 2012/0271557 A1 | 10/2012 | Sekimoto et al. |
| 2012/0296311 A1 | 11/2012 | Brauker et al. |
| 2013/0004844 A1 | 1/2013 | Hosoe et al. |
| 2013/0030841 A1 | 1/2013 | Bergstrom et al. |
| 2013/0035575 A1 | 2/2013 | Mayou et al. |
| 2013/0035865 A1 | 2/2013 | Mayou et al. |
| 2013/0035871 A1 | 2/2013 | Mayou et al. |
| 2013/0047084 A1 | 2/2013 | Sanders et al. |
| 2013/0171938 A1 | 7/2013 | Mears et al. |
| 2013/0184547 A1 | 7/2013 | Taub et al. |
| 2013/0184996 A1 | 7/2013 | Zivitz et al. |
| 2013/0197479 A1 | 8/2013 | Butler et al. |
| 2013/0211248 A1 | 8/2013 | Cowan et al. |
| 2013/0291116 A1 | 10/2013 | Homer |
| 2013/0298063 A1 | 11/2013 | Joy et al. |
| 2013/0310756 A1 | 11/2013 | Whalley et al. |
| 2013/0331659 A1 | 12/2013 | Koski et al. |
| 2013/0338453 A1 | 12/2013 | Duke et al. |
| 2014/0012117 A1 | 1/2014 | Mensinger et al. |
| 2014/0012118 A1 | 1/2014 | Mensinger et al. |
| 2014/0012510 A1 | 1/2014 | Mensinger et al. |
| 2014/0012511 A1 | 1/2014 | Mensinger et al. |
| 2014/0018733 A1 | 1/2014 | Sjoelund et al. |
| 2014/0019396 A1 | 1/2014 | Carlsgaard et al. |
| 2014/0025400 A1 | 1/2014 | Galley et al. |
| 2014/0058749 A1 | 2/2014 | Galley et al. |
| 2014/0068487 A1 | 3/2014 | Steiger et al. |
| 2014/0074041 A1 | 3/2014 | Pedersen et al. |
| 2014/0081662 A1 | 3/2014 | Bradrick et al. |
| 2014/0091941 A1 | 4/2014 | Johnson et al. |
| 2014/0113856 A1 | 4/2014 | Pohl et al. |
| 2014/0114161 A1 | 4/2014 | Kamath et al. |
| 2014/0128705 A1 | 5/2014 | Mazlish |
| 2014/0148659 A1 | 5/2014 | Sloan et al. |
| 2014/0187889 A1 | 7/2014 | Cohen et al. |
| 2014/0200426 A1 | 7/2014 | Taub et al. |
| 2014/0207080 A1 | 7/2014 | Allerdings |
| 2014/0257065 A1 | 9/2014 | Brister et al. |
| 2014/0276531 A1 | 9/2014 | Walsh |
| 2014/0288494 A1 | 9/2014 | Brister et al. |
| 2014/0297299 A1 | 10/2014 | Lester, IV |
| 2014/0309615 A1 | 10/2014 | Mazlish |
| 2014/0324020 A1 | 10/2014 | Stefansen |
| 2014/0371682 A1 | 12/2014 | Bengtsson et al. |
| 2015/0018770 A1 | 1/2015 | Baran et al. |
| 2015/0043410 A1 | 2/2015 | Chaturvedi et al. |
| 2015/0073337 A1 | 3/2015 | Saint et al. |
| 2015/0151050 A1 | 6/2015 | Estes |
| 2015/0164415 A1 | 6/2015 | Bashan et al. |
| 2015/0193595 A1 | 7/2015 | Mcnamara et al. |
| 2015/0202375 A1 | 7/2015 | Schabbach et al. |
| 2015/0202377 A1 | 7/2015 | Haupt |
| 2015/0205947 A1 | 7/2015 | Berman et al. |
| 2015/0246179 A1 | 9/2015 | Zur et al. |
| 2015/0260726 A1 | 9/2015 | Refvik |
| 2015/0289823 A1 | 10/2015 | Rack-Gomer et al. |
| 2015/0290396 A1 | 10/2015 | Nagar et al. |
| 2015/0306304 A1 | 10/2015 | Schabbach et al. |
| 2015/0350147 A1 | 12/2015 | Shepherd et al. |
| 2015/0351683 A1 | 12/2015 | Brauker et al. |
| 2015/0356273 A1 | 12/2015 | Cave |
| 2015/0359490 A1 | 12/2015 | Massey et al. |
| 2015/0359965 A1 | 12/2015 | O'Connor et al. |
| 2015/0365826 A1 | 12/2015 | Mancini et al. |
| 2016/0030673 A1 | 2/2016 | White et al. |
| 2016/0030679 A1 | 2/2016 | Nielsen et al. |
| 2016/0030680 A1 | 2/2016 | Veasey et al. |
| 2016/0030683 A1 | 2/2016 | Taylor et al. |
| 2016/0038675 A1 | 2/2016 | Estes et al. |
| 2016/0047685 A1 | 2/2016 | Blei et al. |
| 2016/0047743 A1 | 2/2016 | Blei et al. |
| 2016/0051760 A1 | 2/2016 | Krusell et al. |
| 2016/0065799 A1 | 3/2016 | Haupt et al. |
| 2016/0066843 A1 | 3/2016 | Mensinger et al. |
| 2016/0081632 A1 | 3/2016 | Kamath et al. |
| 2016/0082192 A1 | 3/2016 | Veasey et al. |
| 2016/0101232 A1 | 4/2016 | Kamath et al. |
| 2016/0101234 A1 | 4/2016 | Bock et al. |
| 2016/0106927 A1 | 4/2016 | Moeller et al. |
| 2016/0113558 A1 | 4/2016 | Bhavaraju et al. |
| 2016/0117481 A1 | 4/2016 | Booth et al. |
| 2016/0155081 A1 | 6/2016 | Legisa et al. |
| 2016/0213848 A1 | 7/2016 | Whalley et al. |
| 2016/0223380 A1 | 8/2016 | Whalley et al. |
| 2016/0235925 A1 | 8/2016 | Kuhn et al. |
| 2016/0263327 A1 | 9/2016 | Radmer et al. |
| 2016/0266752 A1 | 9/2016 | Wu et al. |
| 2016/0287804 A1 | 10/2016 | Madsen et al. |
| 2016/0287807 A1 | 10/2016 | Madsen et al. |
| 2016/0324463 A1 | 11/2016 | Simpson et al. |
| 2017/0028141 A1* | 2/2017 | Fiedler .................. A61M 5/003 |
| 2017/0053101 A1 | 2/2017 | Booth et al. |
| 2017/0053552 A1 | 2/2017 | Zhong et al. |
| 2017/0056605 A1* | 3/2017 | Kondo .................. A61M 5/427 |
| 2017/0068799 A1 | 3/2017 | Mensinger et al. |
| 2017/0103175 A1 | 4/2017 | Chopra et al. |
| 2017/0106052 A1 | 4/2017 | Spat et al. |
| 2017/0124275 A1 | 5/2017 | Reihman et al. |
| 2017/0131993 A1 | 5/2017 | Salameh et al. |
| 2017/0132120 A1 | 5/2017 | Salameh et al. |
| 2017/0132392 A1 | 5/2017 | Gerken |
| 2017/0138769 A1 | 5/2017 | Jones et al. |
| 2017/0139974 A1 | 5/2017 | Javed et al. |
| 2017/0151390 A1 | 6/2017 | Muller-Pathle |
| 2017/0173261 A1 | 6/2017 | O'Connor et al. |
| 2017/0181645 A1 | 6/2017 | Mahalingam et al. |
| 2017/0181678 A1 | 6/2017 | Newberry |
| 2017/0182258 A1 | 6/2017 | Michael |
| 2017/0185283 A1 | 6/2017 | Bhavaraju et al. |
| 2017/0185284 A1 | 6/2017 | Bhavaraju et al. |

(56)                    References Cited

U.S. PATENT DOCUMENTS

| | | |
|---|---|---|
| 2017/0189615 A1 | 7/2017 | Estes |
| 2017/0189616 A1 | 7/2017 | Bengtsson et al. |
| 2017/0189625 A1 | 7/2017 | Cirillo et al. |
| 2017/0199985 A1 | 7/2017 | Mazlish et al. |
| 2017/0215811 A1 | 8/2017 | Newberry |
| 2017/0216518 A1 | 8/2017 | Davis et al. |
| 2017/0216524 A1 | 8/2017 | Haider et al. |
| 2017/0219486 A1 | 8/2017 | Blei et al. |
| 2017/0220751 A1 | 8/2017 | Davis et al. |
| 2017/0224922 A1 | 8/2017 | Lepple-Wienhues |
| 2017/0224927 A1 | 8/2017 | Windum et al. |
| 2017/0228518 A1 | 8/2017 | Booth et al. |
| 2017/0232203 A1 | 8/2017 | Krusell |
| 2017/0235919 A1 | 8/2017 | Bauss et al. |
| 2017/0235920 A1 | 8/2017 | Bauss et al. |
| 2017/0251982 A1 | 9/2017 | Koehler et al. |
| 2017/0266389 A1 | 9/2017 | Mcloughlin et al. |
| 2017/0270276 A1 | 9/2017 | Saint et al. |
| 2017/0270829 A1 | 9/2017 | Bauss |
| 2017/0286194 A1 | 10/2017 | Morris et al. |
| 2017/0286614 A1 | 10/2017 | Morris et al. |
| 2017/0286638 A1 | 10/2017 | Searle et al. |
| 2017/0304538 A1 | 10/2017 | Renstad et al. |
| 2017/0304541 A1 | 10/2017 | Bauss et al. |
| 2017/0304552 A1 | 10/2017 | Prager |
| 2017/0312446 A1 | 11/2017 | Kunz et al. |
| 2017/0316178 A1* | 11/2017 | Riedel .................... G16H 20/13 |
| 2017/0338864 A1 | 11/2017 | Rolsted et al. |
| 2017/0340808 A1 | 11/2017 | Andersen et al. |
| 2017/0340826 A1 | 11/2017 | Draper |
| 2017/0351842 A1 | 12/2017 | Booth et al. |
| 2017/0366617 A1 | 12/2017 | Mensinger et al. |
| 2017/0367627 A1 | 12/2017 | Brister et al. |
| 2017/0368263 A1 | 12/2017 | Ploch |
| 2017/0368265 A1 | 12/2017 | Groeschke et al. |
| 2018/0001027 A1 | 1/2018 | Klemm et al. |
| 2018/0008773 A1 | 1/2018 | Hautaviita et al. |
| 2018/0008778 A1 | 1/2018 | Erbstein |
| 2018/0008779 A1 | 1/2018 | Hautaviita et al. |
| 2018/0028759 A1 | 2/2018 | Riedel et al. |
| 2018/0028760 A1 | 2/2018 | Gugl et al. |
| 2018/0036484 A1 | 2/2018 | Andersen |
| 2018/0036495 A1* | 2/2018 | Searle .................... A61M 5/20 |
| 2018/0042559 A1 | 2/2018 | Cabrera et al. |
| 2018/0043104 A1 | 2/2018 | Stephan |
| 2018/0050157 A1 | 2/2018 | Whalley et al. |
| 2018/0060008 A1 | 3/2018 | Bender et al. |
| 2018/0064879 A1 | 3/2018 | Sall et al. |
| 2018/0085532 A1 | 3/2018 | Desborough et al. |
| 2018/0099084 A1 | 4/2018 | Schabbach et al. |
| 2018/0103879 A1 | 4/2018 | Masciotti et al. |
| 2018/0121630 A1 | 5/2018 | Portnoy |
| 2018/0147362 A1 | 5/2018 | Arenas et al. |
| 2018/0154086 A1 | 6/2018 | Toporek et al. |
| 2018/0161505 A1 | 6/2018 | Prager |
| 2018/0185587 A1 | 7/2018 | Brauker et al. |
| 2018/0217917 A1 | 8/2018 | Hayter et al. |
| 2018/0221582 A1 | 8/2018 | Klemm et al. |
| 2018/0224315 A1 | 8/2018 | Schabbacha et al. |
| 2018/0226150 A1 | 8/2018 | Hayter et al. |
| 2018/0228977 A1 | 8/2018 | Schabbach et al. |
| 2018/0236172 A1 | 8/2018 | Schabbach et al. |
| 2018/0236185 A1 | 8/2018 | Sall et al. |
| 2018/0243504 A1 | 8/2018 | Scott et al. |
| 2018/0262578 A1 | 9/2018 | Shaw et al. |
| 2018/0268236 A1 | 9/2018 | Klemm |
| 2018/0272072 A1 | 9/2018 | Radmer et al. |
| 2018/0277246 A1 | 9/2018 | Zhong et al. |
| 2018/0289901 A1 | 10/2018 | Bggild-Damkvist et al. |
| 2018/0296767 A1 | 10/2018 | Sall |
| 2018/0303417 A1 | 10/2018 | Mensinger et al. |
| 2018/0304028 A1 | 10/2018 | Riedel |
| 2018/0326164 A1 | 11/2018 | Bauss et al. |
| 2018/0339113 A1 | 11/2018 | Wendland et al. |
| 2018/0341826 A1 | 11/2018 | Allerdings et al. |
| 2018/0353694 A1 | 12/2018 | Riedel et al. |
| 2018/0353698 A1 | 12/2018 | Saint et al. |
| 2018/0353699 A1 | 12/2018 | Helmer et al. |
| 2018/0353700 A1 | 12/2018 | Sall et al. |
| 2018/0361067 A1 | 12/2018 | Sall et al. |
| 2018/0361076 A1 | 12/2018 | Klemm et al. |
| 2018/0361082 A1 | 12/2018 | Sall et al. |
| 2018/0368683 A1 | 12/2018 | Hu et al. |
| 2018/0369479 A1 | 12/2018 | Hayter et al. |
| 2018/0369488 A1 | 12/2018 | Carlsson et al. |
| 2018/0369490 A1 | 12/2018 | Rehbein et al. |
| 2019/0001060 A1 | 1/2019 | Gylleby et al. |
| 2019/0001069 A1 | 1/2019 | Carlsson et al. |
| 2019/0009032 A1 | 1/2019 | Hautaviita et al. |
| 2019/0015020 A1 | 1/2019 | Brister et al. |
| 2019/0015596 A1 | 1/2019 | Saint et al. |
| 2019/0022320 A1 | 1/2019 | Carlsson et al. |
| 2019/0029590 A1 | 1/2019 | Baran et al. |
| 2019/0030250 A1 | 1/2019 | Steel et al. |
| 2019/0035500 A1 | 1/2019 | Saint et al. |
| 2019/0036688 A1 | 1/2019 | Wasily et al. |
| 2019/0076070 A1 | 3/2019 | Nogueira et al. |
| 2019/0125224 A1 | 5/2019 | Kamath et al. |
| 2019/0125969 A1 | 5/2019 | Montgomery et al. |
| 2019/0132801 A1 | 5/2019 | Kamath et al. |
| 2019/0149887 A1 | 5/2019 | Williams et al. |
| 2019/0173885 A1 | 6/2019 | Kamath et al. |
| 2019/0175833 A1 | 6/2019 | Sjolund et al. |
| 2019/0175841 A1 | 6/2019 | Sjolund et al. |
| 2019/0183434 A1 | 6/2019 | Sjolund et al. |
| 2019/0184091 A1 | 6/2019 | Sjolund et al. |
| 2019/0184092 A1 | 6/2019 | Sjolund et al. |
| 2019/0184093 A1 | 6/2019 | Sjolund et al. |
| 2019/0184094 A1 | 6/2019 | Sjolund et al. |
| 2019/0184107 A1 | 6/2019 | Sjolund et al. |
| 2019/0184108 A1 | 6/2019 | Sjolund et al. |
| 2019/0184109 A1 | 6/2019 | Sjolund et al. |
| 2019/0184111 A1 | 6/2019 | Sjolund et al. |
| 2019/0192071 A1 | 6/2019 | Taub et al. |
| 2019/0237181 A1 | 8/2019 | Steinberg |
| 2019/0239825 A1 | 8/2019 | Kumar et al. |
| 2019/0274598 A1 | 9/2019 | Scott et al. |
| 2019/0282141 A1 | 9/2019 | Causey et al. |
| 2019/0314575 A1 | 10/2019 | Wilcox et al. |
| 2020/0016336 A1 | 1/2020 | Patek et al. |
| 2020/0205724 A1 | 7/2020 | Lee et al. |
| 2020/0261649 A1 | 8/2020 | Michaud et al. |
| 2020/0350052 A1 | 11/2020 | Saint et al. |
| 2020/0360794 A1 | 11/2020 | Intonato et al. |

FOREIGN PATENT DOCUMENTS

| | | |
|---|---|---|
| CN | 103443798 A | 12/2013 |
| CN | 103957961 A | 7/2014 |
| CN | 104411349 A | 3/2015 |
| CN | 104797282 A | 7/2015 |
| CN | 105377118 A | 3/2016 |
| CN | 107073207 A | 8/2017 |
| EP | 0298067 A1 | 1/1989 |
| EP | 0513128 A1 | 11/1992 |
| EP | 0927057 A1 | 7/1999 |
| EP | 1571582 A2 | 9/2005 |
| EP | 1680175 | 7/2006 |
| EP | 2401011 | 1/2012 |
| EP | 2572740 A1 | 3/2013 |
| EP | 2767297 A2 | 8/2014 |
| EP | 2911717 | 9/2015 |
| EP | 2926846 A1 | 10/2015 |
| EP | 3049132 A1 | 8/2016 |
| EP | 2879740 B1 | 3/2017 |
| EP | 3167393 A2 | 5/2017 |
| EP | 2797660 B1 | 10/2019 |
| JP | 2014-514046 A | 6/2014 |
| JP | 2014-531283 A | 11/2014 |
| JP | 2015-178044 A | 10/2015 |
| JP | 2016-515452 A | 5/2016 |
| JP | 2016-517601 A | 6/2016 |
| JP | 6058673 B2 | 1/2017 |
| WO | 85/02544 A1 | 6/1985 |

(56)        References Cited

FOREIGN PATENT DOCUMENTS

| WO | 91/10460 | A1 | 7/1991 |
|---|---|---|---|
| WO | 96/38190 | A1 | 12/1996 |
| WO | 98/10813 | A1 | 3/1998 |
| WO | 2005/046559 | A2 | 5/2005 |
| WO | 2010/037828 | A1 | 4/2010 |
| WO | 2010/052275 | A2 | 5/2010 |
| WO | 2010/056718 | A2 | 5/2010 |
| WO | 2010/098927 | A1 | 9/2010 |
| WO | 2011/041007 | A1 | 4/2011 |
| WO | 2011/091238 | A1 | 7/2011 |
| WO | 2012/046199 | A1 | 4/2012 |
| WO | 2013/004844 | A1 | 1/2013 |
| WO | 2013/037754 | A2 | 3/2013 |
| WO | 2013/053695 | A1 | 4/2013 |
| WO | 2013/177135 | A1 | 11/2013 |
| WO | 2014/020010 | A2 | 2/2014 |
| WO | 2014/029621 | A1 | 2/2014 |
| WO | 2014/064691 | A2 | 5/2014 |
| WO | 2014/128157 | A1 | 8/2014 |
| WO | 2015/047870 | A1 | 4/2015 |
| WO | 2015/169814 | A1 | 11/2015 |
| WO | 2015/185686 | A1 | 12/2015 |
| WO | 2016/004210 | A1 | 1/2016 |
| WO | 2016/019192 | A1 | 2/2016 |
| WO | 2016/007935 | A3 | 4/2016 |
| WO | 2016/071912 | A1 | 5/2016 |
| WO | 2016/116853 | A1 | 7/2016 |
| WO | 2016/151973 | A1 | 9/2016 |
| WO | 2017/123523 | A1 | 7/2017 |
| WO | 2017/123525 | A1 | 7/2017 |
| WO | 2017/132557 | A1 | 8/2017 |
| WO | 2017/132577 | A1 | 8/2017 |
| WO | 2018/064222 | A1 | 4/2018 |

OTHER PUBLICATIONS

Baker, New Technologies for Diabetes, Mar. 25, 2017, XP055568829, 76, https://diabetes-education.com/wp-content/uploads/2017/03/Baker-HCP3.pdf.
Cision PR News Wire, "Companion Medical Announces Insights by InPen, the Future of MDI Reports", Jun. 20, 2018.
Hu et al., An Improved PID Algorithm Based on Insulin-on-Board Estimate for Blood Glucose Control with Type 1 Diabetes, Jan. 1, 2015, Computational and Mathematical Methods in Medicine, 1-8, 2015.
Near Field Communication versus Bluetooth, Jan. 3, 2016, NearFieldCommunication.org via web.archive.org (Year: 2016).
Sara Krugman, Bionic Pancreas User Interface (3/4): Interface Details, Tidepool.org, Jul. 20, 2015.
T:slimx2 Insulin Pump User Guide, Tandem Diabetes Care, Jul. 22, 2016.
White, Common Sensing, May 2, 2017, XP055568837, 15, Mar. 13, 2019.
Australian Patent Examination Report No. 1 for Australian Application No. 2018383743, dated Oct. 23, 2023, 5 pages.
Chinese First Office Action and Search Report for Chinese Application No. 201880080537.X, dated Apr. 27, 2023, 53 pages with translation.
Chinese First Office Action and Search Report for Chinese Application No. 201880080699.3, dated May 11, 2023, 47 pages with translation.
Chinese Second Office Action for Chinese Application No. 201880080537.X, dated Nov. 10, 2023, 44 pages with translation.
Communication pursuant to Article 94(3) EPC for European Patent Application No. 18 852 783.2, mailed Jun. 22, 2023, 9 pages.
European Communication pursuant to Article 94(3) EPC for European U.S. Appl. No. 18/839,959, dated Apr. 4, 2023, 6 pages.
European Communication pursuant to Article 94(3) EPC for European Application No. 18839960.4, dated May 26, 2023, 6 pages.
European Communication pursuant to Article 94(3) EPC for European Application No. 18839961.2, dated Mar. 22, 2021, 8 pages.
European Examination Report for EP Application No. 18840106.1, mailed Mar. 24, 2023, 14 pages.
European Search Report and Search Opinion Received for EP Application No. 21212980.3, dated on Jul. 7, 2022, 10 pages.
Indian Patent Examination Report for Indian Application No. 202027023258 dated May 19, 2022, 6 pages with English translation.
International Search Report from International Application No. PCT/US2018/065082, mailed Mar. 14, 2019, 5 pages.
International Written Opinion from International Application No. PCT/US2018/065082, mailed Mar. 14, 2019, 8 pages.
Japanese Notice of Reasons for Refusal for Japanese Patent Application No. 2020-551774, dated Dec. 4, 2023, 14 pages with English translation.
Japanese Notice of Reasons for Rejection for Japanese Application No. 2020-551774, dated Sep. 25, 2023, 6 pages with English translation.
International Search Report from International Application No. PCT/US2021/071616, mailed Jan. 19, 2022, 5 pages.
International Written Opinion from International Application No. PCT/US2021/071616, mailed Jan. 19, 2022, 7 pages.

* cited by examiner

INJECTION SITE DETERMINATION SYSTEMS AND METHODS FOR INJECTION SITE TRACKING AND RECOMMENDING INJECTION SITES

CROSS-REFERENCE TO RELATED APPLICATION

This application claims the benefit under 35 U.S.C. § 119(e) of U.S. Provisional Patent Application Ser. No. 63/086,847, filed Oct. 2, 2020, the disclosure of which is hereby incorporated herein in its entirety by this reference.

TECHNICAL FIELD

This disclosure relates generally to methods of improving insulin delivery including an injection site determination system for recommending injection sites during insulin therapy.

BACKGROUND

Diabetes mellitus is a chronic metabolic disorder caused by the inability of a person's pancreas to produce sufficient amounts of the hormone insulin such that the person's metabolism is unable to provide for the proper absorption of sugar and starch. The inability to absorb those carbohydrates sometimes leads to hyperglycemia, i.e., the presence of an excessive amount of glucose within the blood plasma. Hyperglycemia has been associated with a variety of serious symptoms and life threatening long-term complications such as dehydration, ketoacidosis, diabetic coma, cardiovascular diseases, chronic renal failure, retinal damage and nerve damages with the risk of amputation of extremities.

Often, a permanent therapy is necessary to maintain a proper blood glucose level within normal limits. Maintaining a proper glucose level is achieved by regularly supplying insulin to a person with diabetes (PWD). Maintaining a proper blood glucose level creates a significant cognitive burden for a PWD and affects many aspects of the PWD's life. For example, the cognitive burden on a PWD may be attributed to, among other things, tracking meals and constant check-ins and minor course corrections of blood glucose levels. The adjustments of blood glucose levels by a PWD may include taking insulin, tracking insulin dosing and glucose, deciding how much insulin to take, how often to take it, where to inject the insulin, and how to time insulin doses in relation to meals and/or glucose fluctuations. The foregoing factors make up just a portion of the significant cognitive burden of a PWD.

The following example of a typical daily routine for a PWD further illustrates the significant cognitive burden of a PWD. In the morning, the first thoughts/actions by a PWD is often related to their glucose, such as, what is their blood glucose level? How was their blood glucose level overnight? And how are they currently feeling? Upon checking their blood glucose levels (e.g., using a blood glucose meter or monitor), a PWD may then consider what actions to take, such as adjusting their morning activities, changing when or what to eat for breakfast, or determining to take rapid-acting (RA) insulin and deciding where to injection the rapid-acting (RA) insulin. Before they even eat breakfast (or any meal), a PWD considers the amount of food and types of food they plan to eat, perhaps modifying their RA insulin dose based on the carbohydrate content of the food they choose to eat. Before they administer RA insulin, the PWD will try to remember when they took their last dose of insulin, what happened the last time they ate a particular meal and how they felt.

Before leaving the house, a PWD considers, among other things, whether they have enough supplies for glucose monitoring or insulin dosing. This may include batteries, charged devices, backup supplies, glucose testing supplies, and insulin supplies to treat for high blood glucose levels. Additionally, a PWD needs to consider any physical activities (e.g., walking kids to school, going to the gym, riding a bike) that will affect their glucose because exercise may cause their blood glucose to go lower than expected. Even before driving a vehicle, a PWD checks their glucose to determine if it is at a safe level for driving.

As lunchtime approaches, a PWD considers their glucose prior to eating lunch, such as what time they may expect to eat, what they expect to eat throughout the day. As such, a PWD tallies up the carbohydrates and adjusts insulin doses in their head. A PWD also considers what insulin doses were recently taken and whether those doses may still be working to lower blood glucose. This is all done in parallel with whatever they are doing in their busy day, and so the PWD often forgets or fails to fully consider all of the factors described above.

Throughout the day, a PWD often checks glucose levels, especially on days when their activities vary from a typical day. This constant thinking, checking, planning may be exhausting, especially when each check requires decisions, math, and possible behavior changes. Additionally, during the day, a PWD may check inventory on supplies, speak with a health care provider (HCP), refill prescriptions, and contact their health insurance to discuss their therapy and/or supplies.

In the evening, a PWD may have to take a daily insulin dose of long-acting (LA) insulin. Additionally, the PWD may determine if their glucose is holding steady before they fall asleep. If they use an infusion pump, they have to check if their insulin pump is low on insulin and whether they need to refill it before sleep. If they have a continuous glucose monitor, they have to check and see if it is working. Even then, based on what they ate for dinner, the nighttime insulin might not keep their glucose steady. Glucose levels in the night may interfere with sleep as well as add anxiety that could disrupt sleep.

Accordingly, managing diabetes requires significant attention to detail throughout the day. Even with careful planning and self-monitoring, a PWD may skip doses, double dose, or dose the wrong amount and/or type of insulin. Insufficient insulin may result in hyperglycemia, and too much insulin may result in hypoglycemia, which may result in clumsiness, trouble talking, confusion, loss of consciousness, seizures, or death.

In order to assist with self-treatment, some diabetes treatment devices (e.g., blood glucose meters, insulin pumps, without limitation) are equipped with insulin bolus calculators that have the user input an estimate (e.g., numerical estimate) of the quantity of carbohydrates consumed or about to be consumed (or additionally or alternatively protein, fat, or other meal data) and the bolus calculator outputs a recommended size for the insulin bolus dosage. Although bolus calculators remove some of the mental calculations made by the user in determining an appropriate insulin bolus dosage, bolus calculators still burden the user with the mental task of evaluating the constituents of their meal, may require the use of a secondary device, and often require manual entry of data.

Although conventional dosing systems may remove some of the mental burdens for the PWD in determining an appropriate recommendation related to insulin dosing, dosing systems still burden the PWD with one or more of the mental tasks of manually evaluating therapy data, manually determining a dosing recommendation, manually determining injection sites, and manual entry of data.

For convenience or other reasons, the PWD will inject insulin at the same site over numerous injections. Repetitive injections at a same injection site may cause buildup of scar tissue and fat, which may cause lipohypertrophy. Lipohypertrophy is a lump under the skin, caused by an accumulation of extra fat at the site of numerous subcutaneous injections of insulin. Lipohypertrophy may be unsightly, painful, and may change a timing and/or completeness of insulin action. PWD often fail to properly rotate their injection sites and have their favorite (e.g., less painful or more comfortable) areas for injecting insulin. As a result, Lipohypertrophy is a relatively common issue and negatively affects insulin therapy.

BRIEF SUMMARY

The various embodiments described below provide benefits and/or solve one or more of the foregoing or other problems in the art with systems and methods for determining and recommending injection sites. Some embodiments include a method of improving insulin delivery. The method may include detecting a dosing event of an upcoming insulin dose, identifying a next injection site to recommend to a user for the upcoming insulin dose, and transmitting a recommended injection site to a delivery device to be displayed on the delivery device.

Some embodiments include system for improving insulin delivery. The system may include at least one processor and at least one non-transitory computer-readable storage medium storing instructions thereon that, when executed by the at least one processor, cause the system t responsive to an upcoming insulin dose, identify a next injection site to recommend to a user for the upcoming insulin dose and transmit a recommended injection site to a delivery device to be displayed on the delivery device.

One or more embodiments include a non-transitory computer-readable medium storing instructions thereon that, when executed by at least one processor, cause the at least one processor to perform steps comprising generating an injection site recommendation profile based at least partially on user selected injection sites and a user selection injection cycle, receiving an indication of an upcoming insulin dose, responsive to the indication of the upcoming insulin dose, identifying a next injection site to recommend to a user for the upcoming insulin dose, and transmitting a recommended injection site to a delivery device to be displayed on the delivery device.

BRIEF DESCRIPTION OF THE DRAWINGS

Various embodiments will be described and explained with additional specificity and detail through the use of the accompanying drawings in which.

4

Figure 2A:
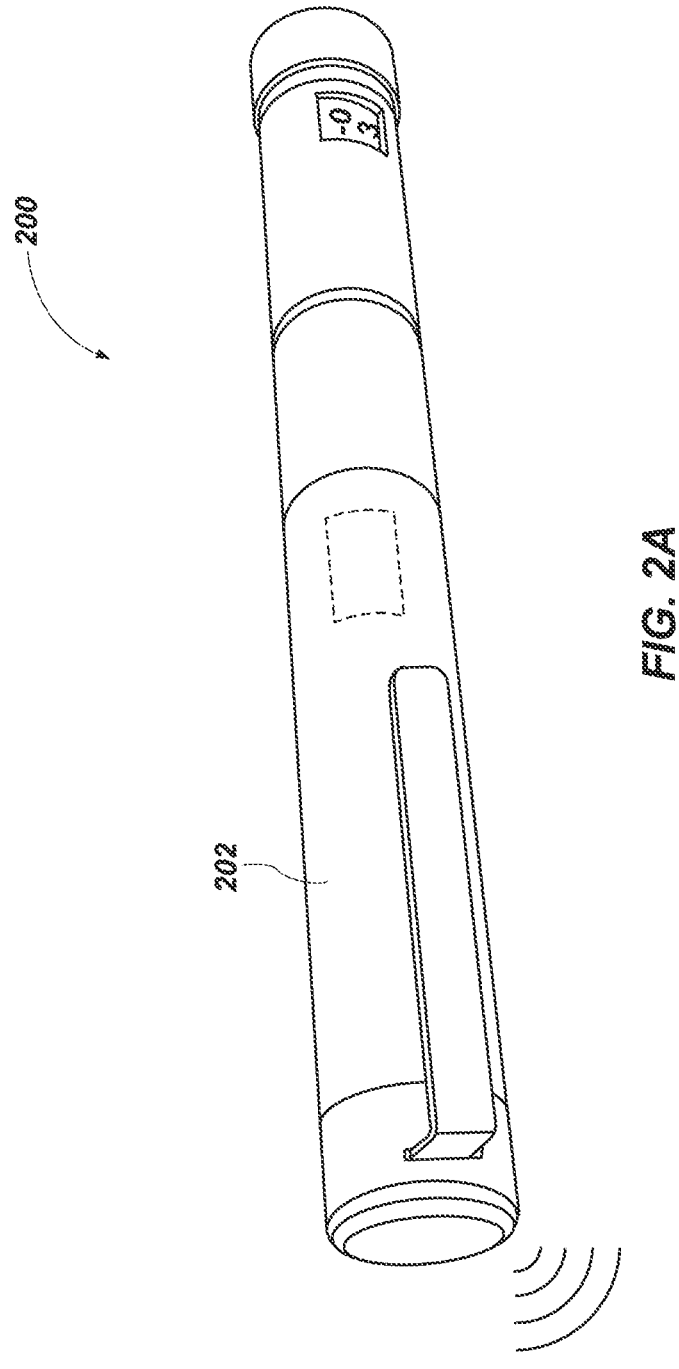
FIG. 2A illustrates a delivery device in accordance with one or more embodiments.
Figure 3:
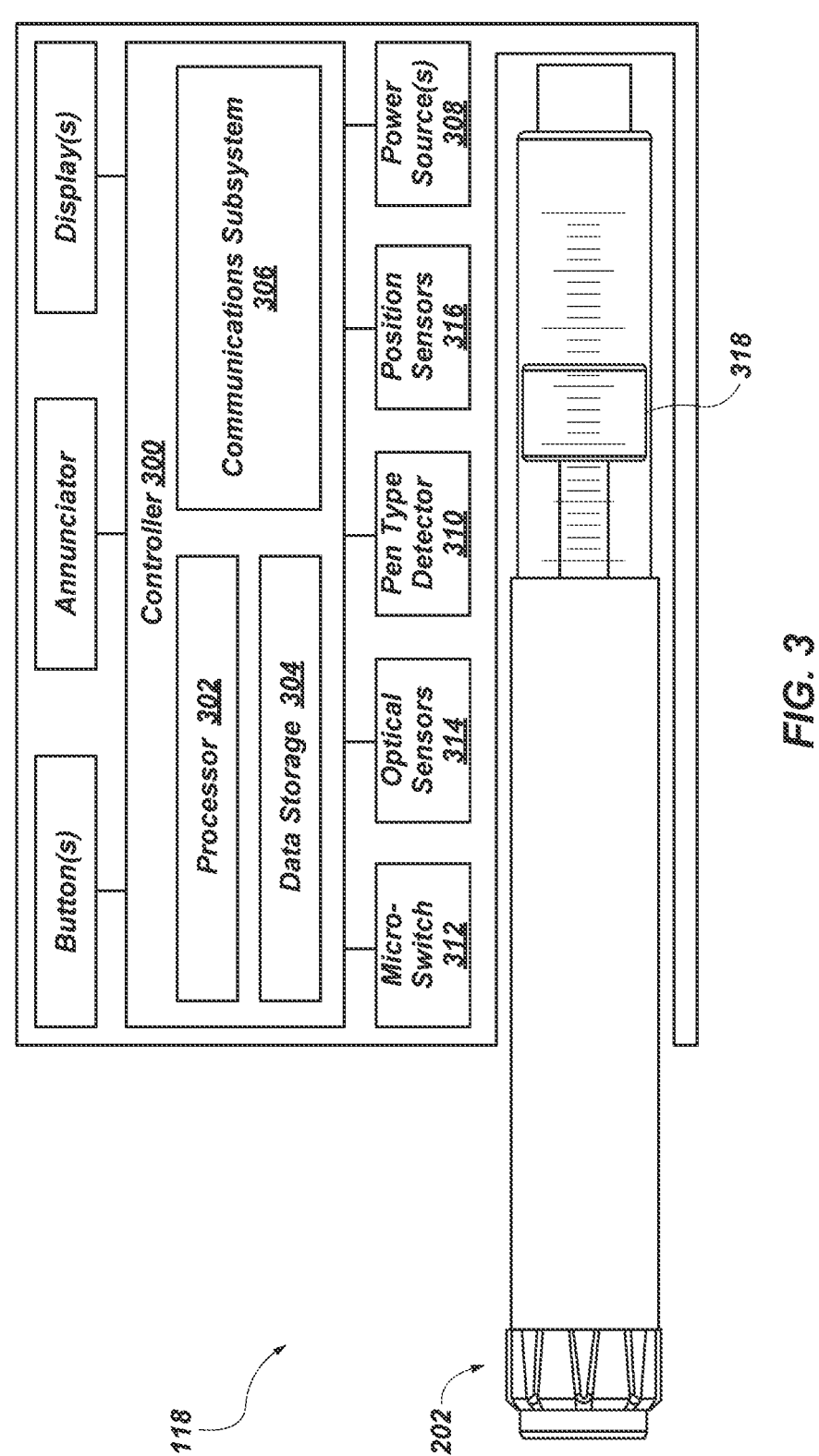
Figure 4A:
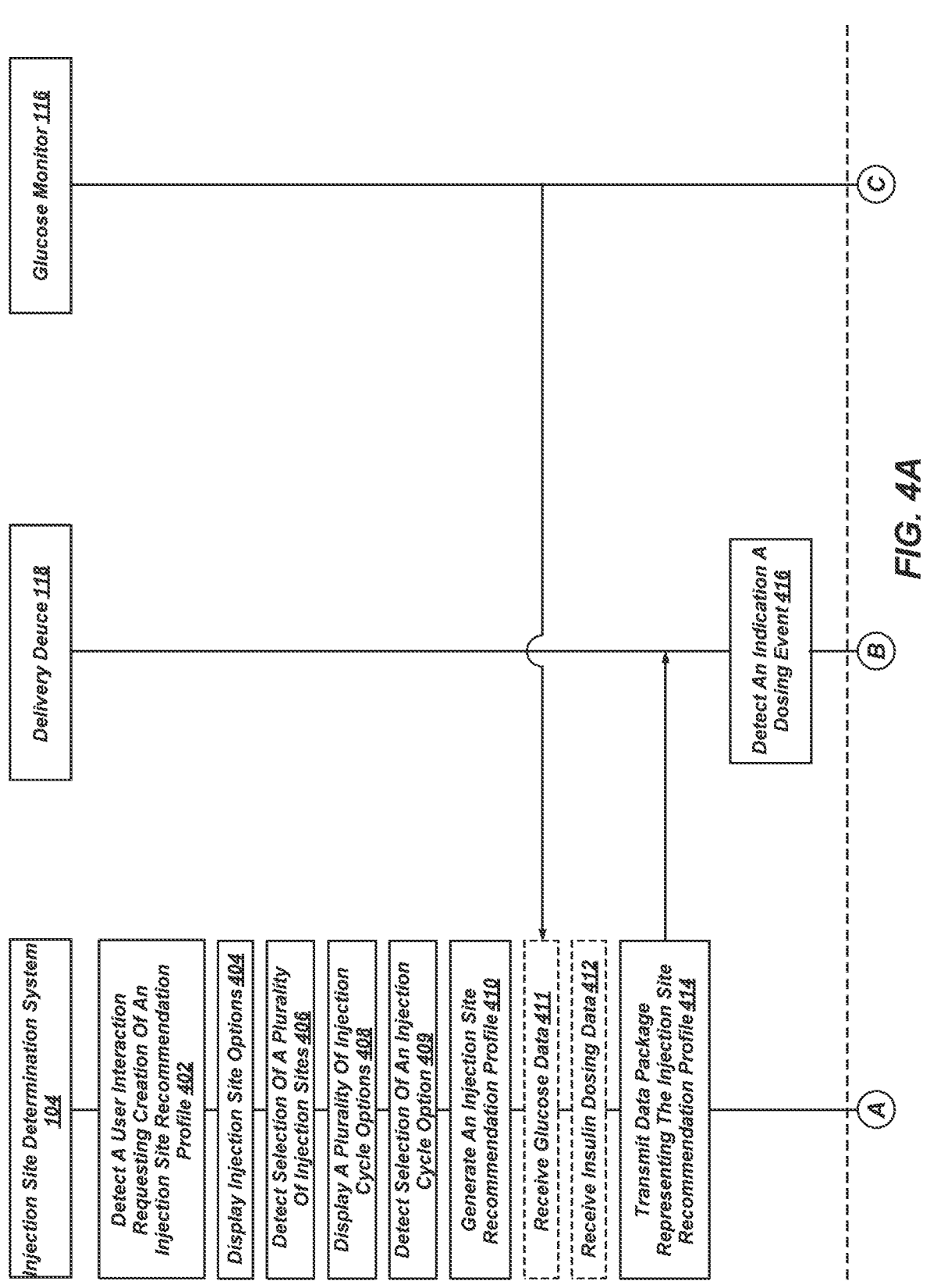
Figure 4B:
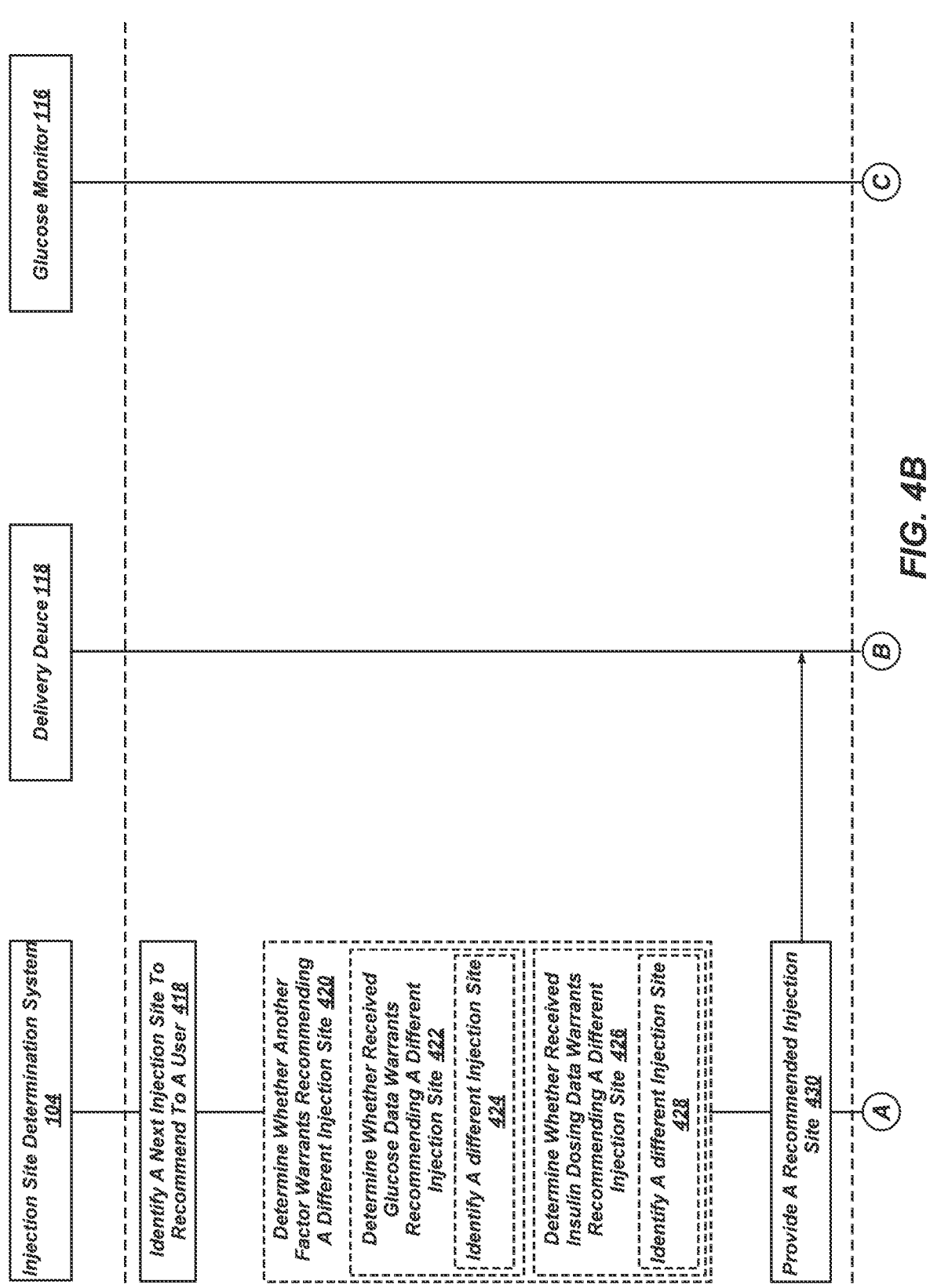
Figure 4C:
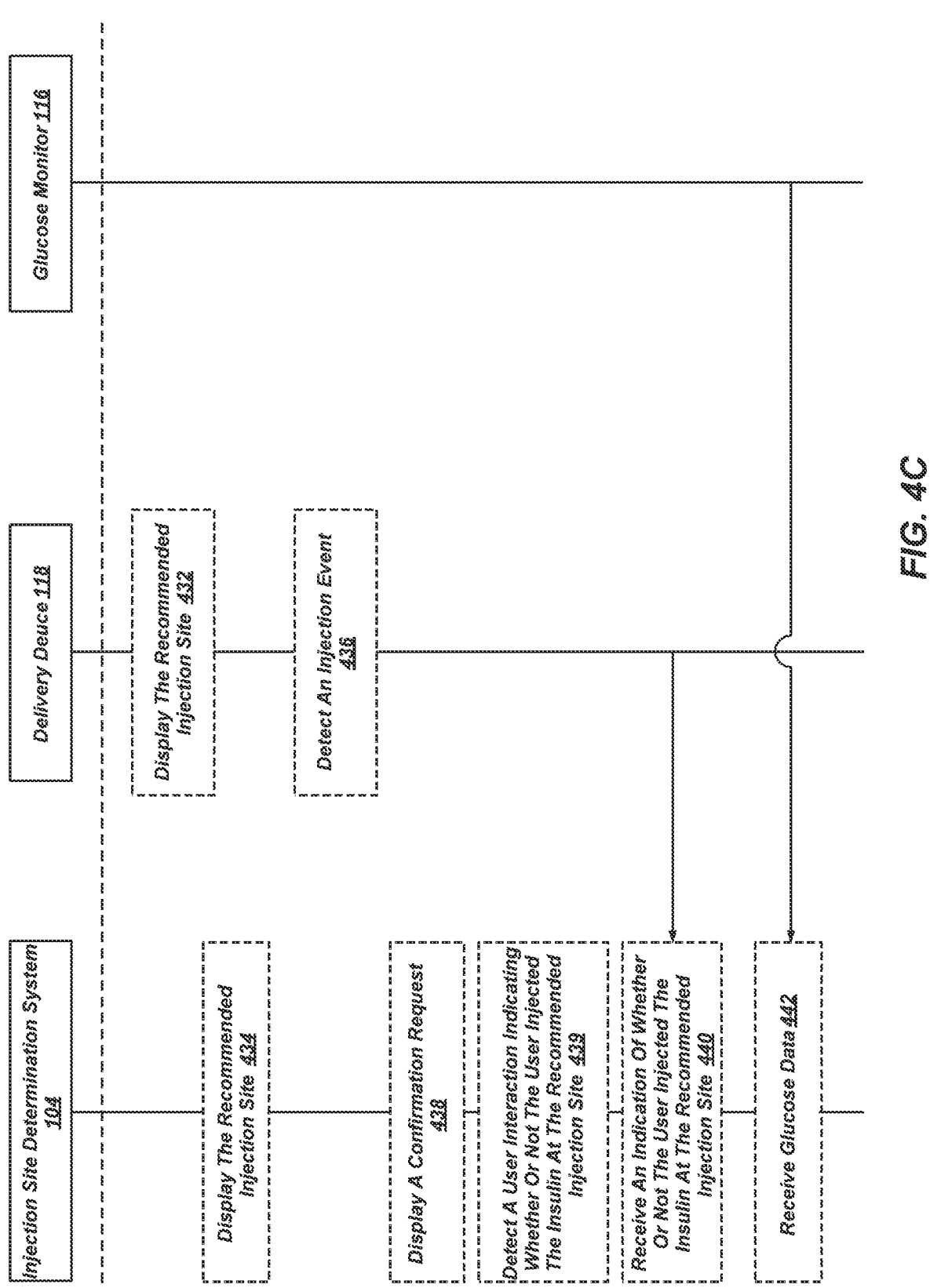
Figure 5:
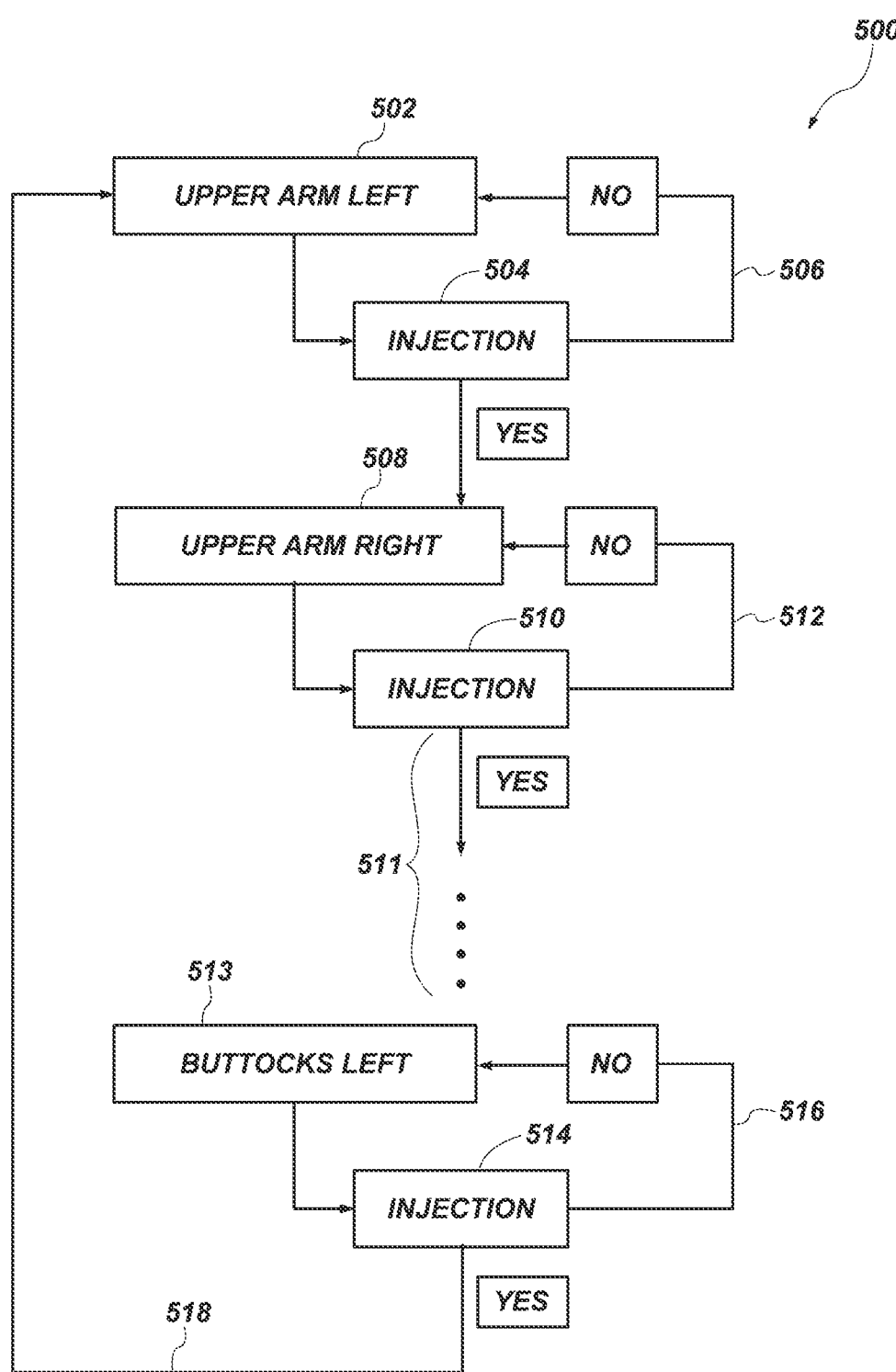
Figure 7:
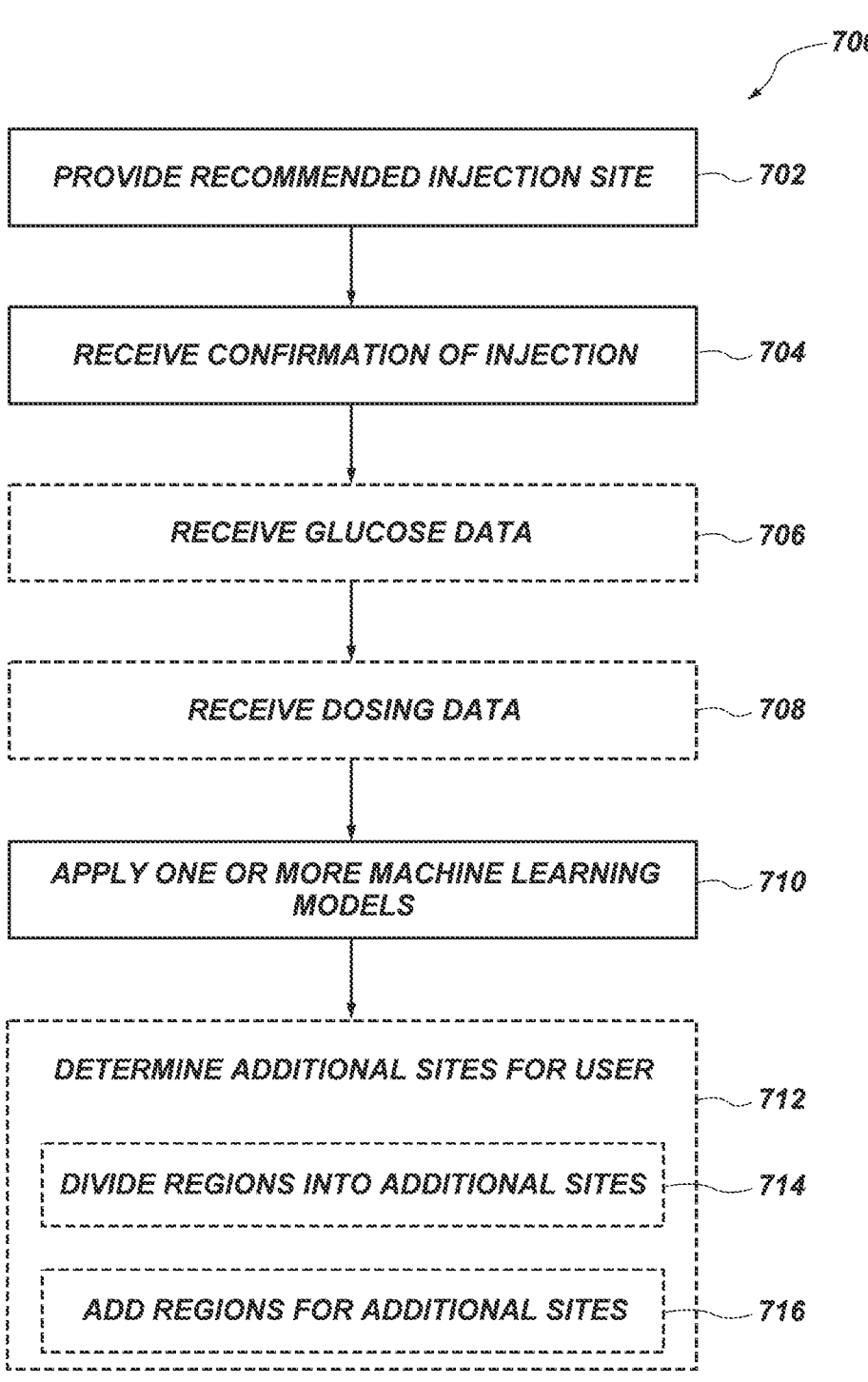
Figure 8:
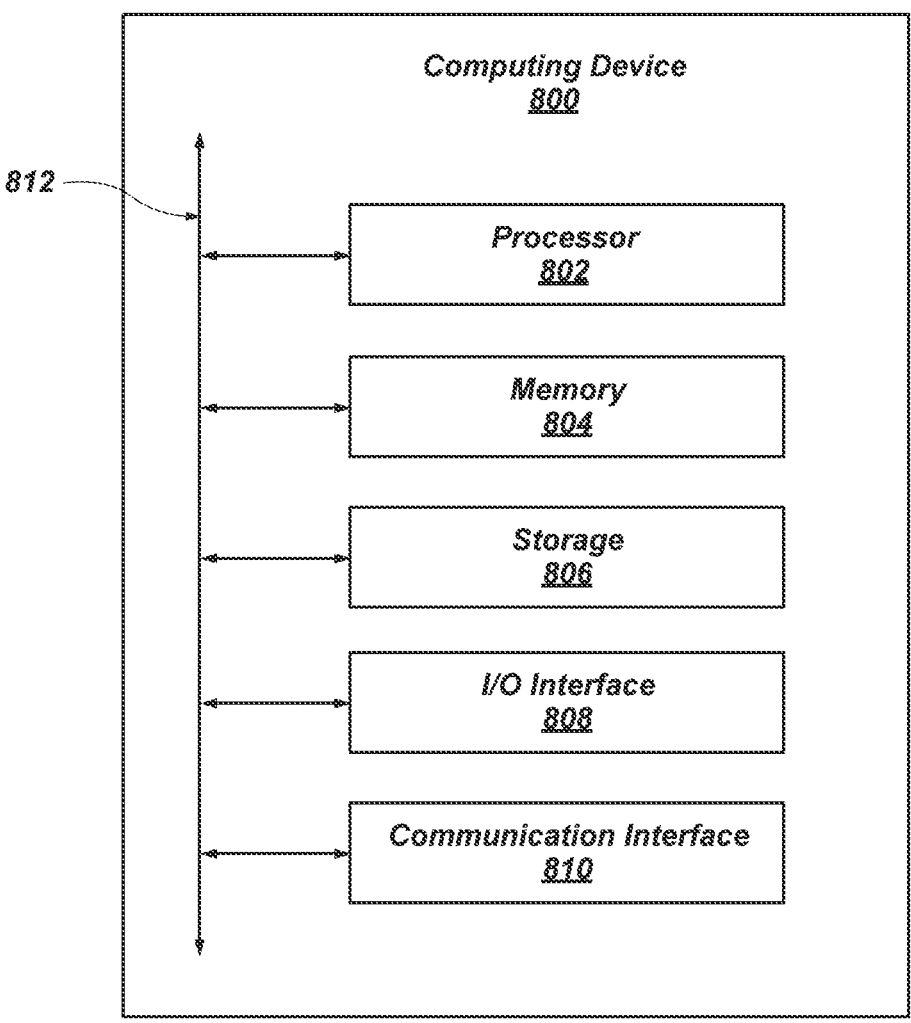

FIG. 3 is a schematic representation of the delivery device of FIG. 2A according to one or more embodiments;

FIGS. 4A-4C illustrate a sequence flow diagram that an injection site determination system may utilize to track and recommend injection site in accordance with one or more embodiments;

FIG. 5 illustrates a simplified flow chart of a method of determining an injection site to recommend according to one or more embodiments;

FIGS. 6A-6E illustrate a plurality of schematic representations of graphical user interfaces of the injection site determination system (e.g., an application of the injection site determination system) that a user may utilize to create an injection site recommendation profile according to one or more embodiments;

FIG. 7 illustrates a simplified flow chart of a method of determining additional injection sites to recommend to the user according to one or more embodiments; and FIG. 8 illustrates a block diagram of an exemplary computing device in accordance with one or more embodiments.

DETAILED DESCRIPTION

The illustrations presented herein are not actual views of any particular injection site determination system, or any component thereof, but are merely idealized representations, which are employed to describe the present invention.

As used herein, the singular forms following "a," "an," and "the" are intended to include the plural forms as well, unless the context clearly indicates otherwise.

As used herein, the term "may" with respect to a material, structure, feature, function, or method act indicates that such is contemplated for use in implementation of an embodiment of the disclosure, and such term is used in preference to the more restrictive term "is" so as to avoid any implication that other compatible materials, structures, features, functions, and methods usable in combination therewith should or must be excluded.

As used herein, any relational term, such as "first," "second," etc., is used for clarity and convenience in understanding the disclosure and accompanying drawings, and does not connote or depend on any specific preference or order, except where the context clearly indicates otherwise.

As used herein, the term "substantially" in reference to a given parameter, property, act, or condition means and includes to a degree that one skilled in the art would understand that the given parameter, property, or condition is met with a small degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "about" used in reference to a given parameter is inclusive of the stated value and has the meaning dictated by the context (e.g., it includes the degree of error associated with measure of the given parameter, as well as variations resulting from manufacturing tolerances, etc.).

As is used herein, the term "injection site" refers to a region of a patient's body where a medication (e.g., insulin) may be injected into the patient's body.

Embodiments include an injection site determination and recommendation system (hereinafter "injection site determination system") and methods for recommending injection sites to a user (e.g., PWD) for upcoming insulin doses. For example, the user may identify (e.g., select) injection sites within an application of the injection site determination system that the user wants to utilize during insulin therapy, and the injection site determination system may cycle through the selected injection sites and may cause recommended injection sites to be displayed on a delivery device (e.g., an insulin pen cap) at the time of an insulin dose. In some embodiments, the recommended injection sites may further be determined based at least partially on available insulin dosing data and glucose data.

The injection site determination system and methods described herein may encourage site rotation and may reduce the effects of lipohypertrophy caused by multiple daily injections. As a result, the injection site determination system and methods described herein may improve insulin delivery. Additionally, the injection site determination system and methods may determine a severity of lipohypertrophy at given injection sites based at least partially on received glucose data and recommended injection sites.

Figure 1:
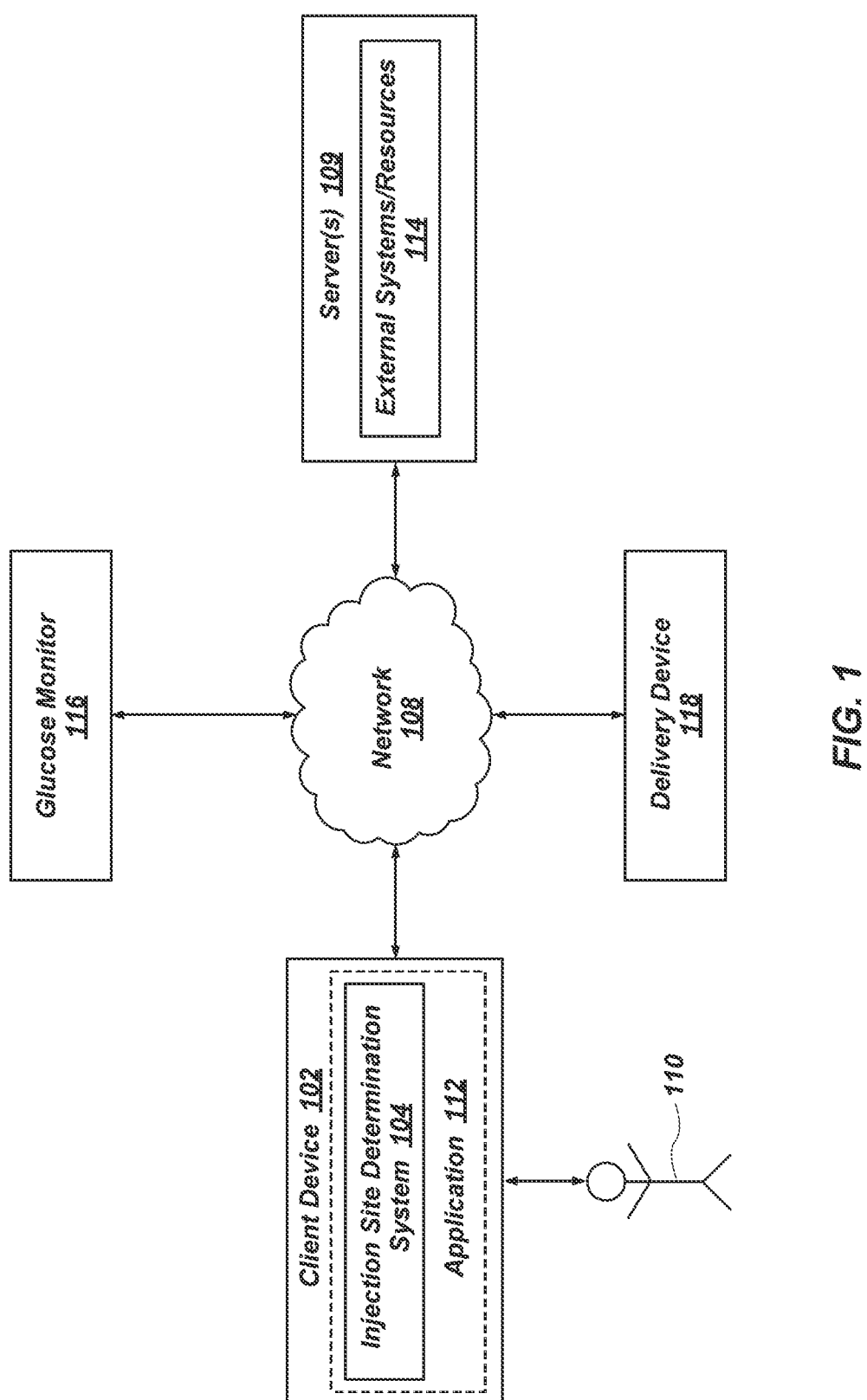
FIG. 1 illustrates a schematic representation of an environment within which an injection site determination system may operate in accordance with one or more embodiments.

FIG. 1 illustrates a schematic diagram of an environment 100 (e.g., an overall system 100) in which an injection site determination and recommendation system (hereinafter "injection site determination system") may operate according to one or more embodiments. As illustrated, the environment 100 includes a client device 102, which may include the injection site determination system 104, at least one server 109 including one or more external systems/resources 114, a network 108, a glucose monitor 116, and a delivery device 118 for delivering medication (e.g., insulin) to a user 110. As is described in greater detail below, the injection site determination system 104 may determine an injection site and recommend an injection site to a user 110 for an upcoming insulin dose based at least partially on one or more factors. For example, the injection site determination system 104 may determine an injection site and recommend an injection site to a user 110 based at least partially on one or more of a predetermined cycle (e.g., a selected pattern), glucose measurements, user preferences, and/or a type and/or an amount of an upcoming insulin dose.

In some embodiments, the client device 102 may include an application 112 (e.g., a tool application) including the injection site determination system 104 or vice versa for enabling users to interact with the injection site determination system 104. For instance, the injection site determination system 104 may form a part of the application 112. As a non-limiting example, the application 112 may be directed to assisting the user 110 in managing insulin therapy of the user 110. In some instances, the application 112 may be a web application for managing insulin therapy of the user 110 and determining and recommending injection sites. In some embodiments, the application 112 may be local to the client device 102. In other embodiments, the application 112 may be stored and/or at least partially operated via a cloud computing service. In additional embodiments, the application 112 may be stored and/or at least partially operated on the delivery device 118. In some embodiments, the client device 102 may execute one or more applications (e.g., application 112) for performing the functions of the various embodiments and processes described herein.

In some embodiments, the injection site determination system 104 may be separate from the client device 102. For example, the injection site determination system 104 may be stored and/or at least partially operated via a cloud computing service (e.g., a server) and may be accessible via the application 112. In one or more embodiments, the injection site determination system 104 may be separate from the application 112 and may interface with the application 112. In some embodiments, the injection site determination system 104 may be stored and/or at least partially operated on the delivery device 118, a cloud computing service, and/or a remote system.

In one or more embodiments, an application 112 may be a native application installed on the client device 102. For example, the application 112 may be a mobile application that installs and runs on a mobile device, such as a smart phone or a tablet. The application 112 may be specific to an operating system of the client device 102. Further, in some embodiments, the application 112 may be a client application that is associated with an injection site determination system 104 and configured to enable interaction directly with an injection site determination system 104 through the application 112.

The client device 102, the glucose monitor 116, the one or more external systems/resources 114, the network 108, and the delivery device 118 may communicate via the network 108. In one or more embodiments, the network 108 may include a combination of cellular or mobile telecommunications networks, a public switched telephone network (PSTN), and/or the Internet or World Wide Web that facilitate the transmission of data between the client device 102 (e.g., the injection site determination system 104), the glucose monitor 116, the one or more external systems/resources 114, the network 108, and the delivery device 118. The network 108, however, may include various other types of networks that use various communication technologies and protocols, such as a wireless local network (WLAN), a wide area network (WAN), a metropolitan area network (MAN), other telecommunication networks, or a combination of two or more of the foregoing networks. In additional embodiments, the client device 102, the glucose monitor 116, the one or more external systems/resources 114, the network 108, and the delivery device 118 may communicate via Bluetooth and Near-field communication in addition to or instead of the network 108.

Although FIG. 1 illustrates a particular arrangement of the client device 102, the glucose monitor 116, the one or more external systems/resources 114, the network 108, and the delivery device 118, various additional arrangements are possible. For example, the delivery device 118, the glucose monitor 116, and/or the one or more external systems/resources 114 may directly communicate with the client device 102 and, accordingly, the injection site determination system 104 and, bypassing the network 108.

As illustrated in FIG. 1, the user 110 may interface with the client device 102, for example, to utilize the injection site determination system 104 in order to select potential injection sites, select injection cycles (e.g., patterns), input user preferences, generate injection site recommendation profiles (e.g., plans), adjust profiles, etc. The user 110 may be an individual (i.e., human user), a business (e.g., employer), a group, or any other entity. Although FIG. 1 illustrates only one user 110 associated with the client device 102, the environment 100 may include any number of a plurality of users that each interact with the environment 100 using a corresponding client device.

The client device 102 may be any one or more of various types of computing devices. For example, the client device 102 may include a mobile device such as a mobile telephone, a smartphone, a PDA, a tablet, or a laptop, or a non-mobile device such as a desktop or another type of computing device. Additional details with respect to the client device 102 are discussed below with respect to FIG. 8.

In some embodiments, the injection site determination system 104 may include one or more systems, servers, and/or other devices for determining and recommending injection sites during an insulin therapy regime. Furthermore, an injection site determination system 104 may include and/or have access to one or more databases. For example, in some embodiments, an injection site determination system 104 may be implemented by a plurality of server devices that store, within the one or more databases, selected injection sites, selected injection cycles, user preferences, glucose measurements, dosing schedules, dosing events, etc. As shown, in some embodiments, an injection site determination system 104 may include a database that stores selected injection sites, selected injection cycles, user preferences, blood glucose measurements, dosing schedules, dosing events, analysis algorithms, etc.

The external systems/resources 114 may include additional systems that interface with the client device 102, the application 112, and/or the injection site determination system 104. For example, in some embodiments, the external systems/resources 114 may include sources of information outside of the environment 100, external entities interacting with the environment 100, and/or other resources. In some embodiments, some or all of the functionality attributed herein to the external systems/resources 114 may be provided by resources included in environment 100. The external systems/resources 114, in some embodiments, may include additional medical devices. The medical devices may include additional insulin delivery systems, including without limitation, insulin delivery devices (e.g., infusion pumps, injection pens, and inhalers), glucose sensors (e.g., CGMs and blood glucose meters), therapy managers (e.g., controllers for controlling open and closed-loop delivery of insulin or aspects of delivering insulin and recommendation systems for providing therapy recommendations to users and/or health providers), and combinations thereof. In some embodiments, the external systems/resources 114 may include subject matter expert input data, clinical literature, conventional medication regimes, etc. The external systems/resources 114, in various embodiments, may include a therapy management system(s). Therapy management systems may include a diabetes management system for monitoring blood glucose data and therapy data and managing therapy settings.

In some embodiments, the glucose monitor 116 may include any known glucose monitor. For example, the glucose monitor may include one or more of a continuous glucose monitor (CGM), a flash glucose monitor, a blood glucose meter (BGM), or any other suitable sensor. In the case of CGMs and flash glucose monitors, the CGMs and flash glucose monitor may provide glucose data based on interstitial fluid glucose levels of a user, which may be correlated to blood glucose levels. A BGM may be configured to provide blood glucose data, typically based on a blood sample. Accordingly, the term "blood glucose" is not limited to using just blood glucose data, values, levels, etc., but is also includes interstitial fluid glucose levels, as well as any intermediate measurement values.

Figure 2B:
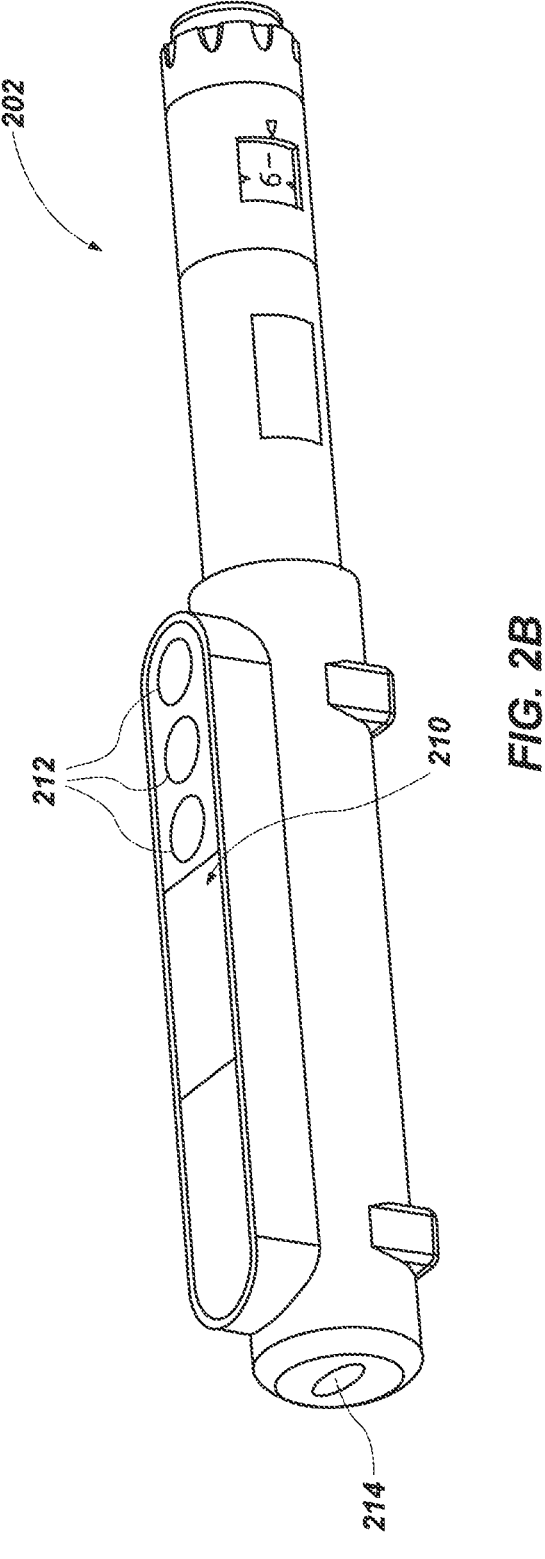
FIG. 2B shows a pen cap of the delivery device of FIG. 2A according to one or more embodiments.

In one or more embodiments, the delivery device 118 may include an insulin pen (e.g., an injection pen). In some embodiments, the delivery device 118 may include one or more of a quick acting insulin (QAI) pen or a long acting insulin (LAI) pen. In other embodiments, the delivery device 118 may include any known insulin pump. FIGS. 2A and 2B show a perspective view of an insulin pen 200 and dose-capture cap 202 according to one or more embodiments. Referring to FIGS. 1-2B together, the insulin pen 200 may include a dose-capture cap 202, which may be in wireless communication with one or more of the client device 102, the application 112, the injection site determination system 104, the glucose monitor 116, and/or the external systems/resources 114. In some embodiments, the insulin pen 200 may include a display screen for displaying dosing information, insulin information, and/or recommendations. The insulin pen may further include one or more inputs (e.g., dials, buttons, and/or touch screen regions) for a user to set a dosage to be delivered. In some embodiments, the insulin pen 200 may itself include dose-capture technology and/or may be in wireless communication with other components of the environment 100.

In some embodiments, the dose-capture cap 202 may include a display screen 210 for displaying one or more of an estimated glucose value (EVG), units for the EVG, a trend indicator for the EVG, a recommended dosage, an identification of the type of insulin, a recommended site injection, a time and amount of a previous dosage, and/or an insulin on board value to remind a user about their most recent dosage. The dose-capture cap 202 may include buttons 212 for inputting meals information, inputting insulin dose information, responding to recommendations, etc. The dose-capture cap 202 may include one or more indicator lights 214, which may light up to indicate that it is transferring data, light up to indicate that the user's attention is needed, and/or light up to indicate whether a dose capture functionality is or is not working. In some embodiments, the display screen 210 of the dose-capture cap 202 may include a touch screen, which may include the one or more buttons 212.

FIG. 3 shows a schematic diagram of the delivery device 118 according to one or more embodiments. Referring to FIGS. 1-4 together, in some embodiments, the dose-capture cap 202 may include a controller 300 including a processor 302, data storage 304 (or memory), and a communications subsystem 306. The communications subsystem 306 may enable wireless communication between the dose-capture cap 202 and the client device 102 and/or a glucose monitor 116. In some instances, the communications subsystem 306 may include a near field communications (NFC) chip. In some instances, the communications subsystem 306 may include a Bluetooth Low Energy (BLE) chip. In some instances, the communications subsystem 306 may include an optical communication device, an infrared communication device, a wireless communication device (such as an antenna), and/or chipset (such as a Bluetooth device (e.g., Bluetooth Low Energy, Classic Bluetooth, etc.), a Near-field communication (NFC) device, an 802.6 device (e.g., Metropolitan Area Network (MAN), a Zigbee device, etc.), a WiFi device, a WiMax device, cellular communication facilities, etc.), and/or the like. In these and other cases, the communications subsystem 306 may exchange data with the network 108 and/or any other device or system described in the present disclosure.

Additionally, in some embodiments, the dose-capture cap 202 may include a power source 308, which may include a rechargeable or non-rechargeable battery. Furthermore, the dose-capture cap may include a pen type detector 310, a micro switch 312, optical sensor(s) 314, and position sensor(s) 316. In one or more embodiments, the controller 300 may determine a pen type from data from the pen type detector 310. The controller 300 may also determine a position of a plunger 318 within the insulin pen 200 using one or more of the micro switch 312, the optical sensor(s) 314, and position sensor(s) 316. Based on the determined positions of the plunger 318, dosing events and/or amounts of insulin delivered may be determined by the controller 300. As a non-limiting example, the delivery device 118 may include any of the insulin delivery pens described in U.S. Pat. No. 10,426,896, issued Oct. 1, 2019, to Desborough et al., the contents and disclosure of which is incorporated herein in its entirety by this reference.

Referring still to FIGS. 1-3 together, as is described in greater detail herein, a user (e.g., a person with diabetes ("PWD")) may use the injection site determination system 104 to receive recommendations and/or reminders regarding an injection site for an upcoming insulin dose (e.g., an impending insulin dose). For example, the injection site determination system 104 may identify an injection site for the user based on or more of a user selected cycle (e.g., pattern), a type of insulin dose, a size of insulin dose, received blood glucose data, data regarding previously administered insulin doses, and/or user preferences and may recommend the injection site to the user. For example, in some embodiments, the injection site determination system 104 may utilize insulin dosing data and site information (e.g., glucose data) for one or more of long acting (LA) insulin sites or rapid acting (RA) insulin sites in determining an injection site for an upcoming injection. Furthermore, the upcoming injection may be either a rapid acting (RA) insulin injection or a long acting (LA) insulin injection. In other words, the injection site determination system 104 may utilize information related to one or more of long acting (LA) insulin site or rapid acting (RA) insulin site in making recommendations for injections sites for one or more of rapid acting (RA) insulin injection or a long acting (LA) insulin injection. In some embodiments, the recommendation and/or reminder may appear on the display screen 210 of the dose-capture cap 202, the display of the insulin delivery pen, and/or a display of the client device 102.

FIGS. 4A-4C illustrate a sequence-flow diagram 400 showing various acts of the injection site determination system 104, the delivery device 118, and the glucose monitor 116 for identifying injections sites for insulin doses for a user, as described herein. The injection site determination system 104 described in regard to FIGS. 4A-4C may be example embodiments of an injection site determination system 104 described in regard to FIGS. 1-3. As noted above in regard to FIG. 1, the injection site determination system 104 may be stored and operated on the client device 102, as part of the application 112 on the client device 102, within a cloud computing service, on the delivery device 118, etc.

As shown in act 402 of FIG. 4A, in some embodiments, an injection site determination system 104 may detect a user interaction requesting creation of an injection site recommendation profile. For example, in some embodiments, the injection site determination system 104 may detect a user interaction via a graphical user interface of the injection site determination system 104 within the application 112. The graphical user interface of the injection site determination system 104 is described in greater detail below in regard to FIGS. 6A-6E.

Responsive to receiving the request to create the injection site recommendation profile, the injection site determination system 104 may display injection site options to potentially be included within the injection site recommendation profile, as shown in act 404 of FIG. 4A. For example, the injection site determination system 104 may display the injection site options within the graphical user interface of the injection site determination system 104 within the application 112. In some embodiments, displaying injection site options includes displaying a schematic representation of a human body with each region of the human body (i.e., injection site option) including a selectable element. In some embodiments, the regions of the human body (i.e., injection site options) may include at least an upper arm right, upper arm left, outer thigh right, outer thigh left, buttocks left, buttocks, right, and abdomen. In some embodiments, each region of the human body may include a single injection site. In other embodiments, one or more of the regions of the human body may include multiple injection sites. For instance, one or more of the regions of the human body may include at least two, three, four, five, or more selection elements as injection sites. Displaying the injection site options is described in greater detail below in regard to FIGS. 6A-6E.

As shown in act 406 of FIG. 4A, the injection site determination system 104 may detect a selection of a plurality of injection sites. In some embodiments, detecting a selection of a plurality of injection sites may include detecting selection of a plurality of selectable elements within the graphical user interface of the injection site determination system 104 within the application 112 of the client device. For example, act 406 may include the injection site determination system 104 detecting a user selecting the plurality of injection sites within the application 112 of the client device 102 (e.g., a mobile device).

Additionally, responsive to detecting the user interaction requesting creation of the injection site recommendation profile, the injection site determination system 104 may display a plurality of injection cycle (e.g., pattern, rotation) options, as shown in act 408 of FIG. 4A. For example, the injection site determination system 104 may display a plurality of injection cycle (e.g., pattern, rotation) options for cycling through the selected injection sites. In some embodiments, the plurality of injection cycles options may include a clockwise cycle, a counter-clock-wise cycle, an alternating cycle, a ping pong cycle, a high to low cycle, a random cycle, etc. In one or more embodiments, the clockwise and counter-clockwise cycles may be relative to the user's body. In other words, a clockwise rotation may include upper arm left, thigh left, thigh right, and upper arm right.

Furthermore, responsive to displaying a plurality of injection cycle (e.g., pattern, rotation) options, the injection site determination system 104 may detect a selection of an injection cycle option, as shown in act 409 of FIG. 4A. In some embodiments, the injection site determination system 104 may enable the user 110 to select a specific user-dictated order of injection sites. In one or more embodiments, the injection site determination system 104 may enable the user 110 to assign user-selected percentages to injection sites such that the injection sites are selected and recommended according to the user-selected percentages. For example, if a given injection site is given a user-selected 33%, the given injection site may be selected and recommended 33% of the time. As a non-limiting example, act 409 may include the injection site determination system 104 detecting a user selecting a clockwise injection cycle. As is discussed in greater detail below, during operation, the injection site determination system 104 may repeat the chosen and/or dictated cycles upon completion.

Responsive to receiving a selection of the plurality of injection sites and a selection of an injection cycle option, the injection site determination system 104 may generate an injection site recommendation profile particular to the user, as shown in act 410 of FIG. 4A. The generated injection site recommendation profile may reflect the selected injection cycle and may be configured to rotate through the plurality of selected injection sites. For example, the generated injection site recommendation profile may include a list of the plurality of selected injection sites, and the list may be ordered based on the selected injection cycle. As a non-limiting example, the generated injection site recommendation profile may include injection sites include upper arm right, upper arm left, thigh right, and thigh left and clockwise rotation. In some embodiments, generating the injection site recommendation profile may include generating a data package representing the injection site recommendation profile. A simplified example process 500 of proceeding through an injection cycle of a plurality of injection sites and identifying recommended injection sites is described in greater detail below in regard to FIG. 5.

In some embodiments, the injection site determination system 104 may optionally receive glucose data from the glucose monitor 116, as show in act 411 of FIG. 4A. In some embodiments, the injection site determination system 104 may receive glucose data for a period of time prior to an upcoming insulin dose. In additional embodiments, the injection site determination system 104 may receive glucose data for a period of time after the upcoming insulin dose. In one or more embodiments, the injection site determination system 104 may continuously receive glucose data from the glucose monitor 116. For example, the injection site determination system 104 may receive glucose data whenever the glucose monitor 116 acquires glucose data (e.g., whenever the glucose monitor 116 performs a glucose measurement). In some embodiments, the injection site determination system 104 may receive glucose data correlating to injections made in one or more of the selected injection sites. For example, after insulin is injected at a respective injection site, the injection site determination system 104 may receive glucose data from a glucose measurement made after the injection and may correlate to the glucose data with the respective injection site. As is discussed below, in some embodiments, the injection site determination system 104 may determine (e.g., identify) an injection site for an upcoming injection based at least partially on the glucose data received from the glucose monitor 116 (or any other source).

In one or more embodiments, the injection site determination system 104 may optionally receive insulin dosing data, as show in act 412 of FIG. 4A. For example, the injection site determination system 104 may receive insulin dosing data from one or more of the delivery device 118, the application 112, and/or the external systems/resources 114. In some embodiments, the insulin dosing data may include an insulin dosing type (e.g., long acting (LA) insulin and rapid acting (RA) insulin), a brand of insulin, a dosing timing, an insulin dosing size, etc. As is discussed below, in some embodiments, the injection site determination system 104 may determine (e.g., identify) an injection site for an upcoming injection based at least partially on the insulin dosing data. For example, in some embodiments, the injection site determination system 104 may utilize insulin dosing data and site information (e.g., glucose data discussed above) for one or more of long acting (LA) insulin sites or rapid acting (RA) insulin sites in determining an injection site for an upcoming injection. Furthermore, the upcoming injection may be either a rapid acting (RA) insulin injection or a long acting (LA) insulin injection. In other words, the injection site determination system 104 may utilize information related to one or more of long acting (LA) insulin site or rapid acting (RA) insulin site in making recommendations for injections sites for one or more of rapid acting (RA) insulin injection or a long acting (LA) insulin injection.

Responsive to generating an injection site recommendation profile, the injection site determination system 104 may transmit a data package representing the injection site recommendation profile to the delivery device 118, as show in act 414 of FIG. 4A. For example, in some embodiments, the injection site determination system 104 may transmit the data package via the network 108, via Bluetooth, or any other wireless, wired, or direct method.

Referring still to FIG. 4A, the delivery device 118 may detect an indication of a dosing event, as shown in act 416. In some embodiments, detecting an indication of a dosing event may include detecting one or more of capping/uncapping of a cap (e.g., a dose-capture cap) from an insulin delivery pen, an actual dosing action, (e.g., detecting insulin delivery, for example, based on a manual action of a pump or a control signal configured to cause insulin delivery), an entry indicating a meal as consumed, and/or a scheduled insulin dose based at least partially on a schedule of insulin dosing. In some embodiments, the delivery device 118 may transmit data representing the indication of the dosing event to the injection site determination system 104. In some embodiments, the injection site determination system 104 may transmit the indication via the network 108, via Bluetooth, or any other wireless, wired, or direct method.

Responsive to detecting an indication of a dosing event, one or more of the delivery device 118 or the injection site determination system 104 may identify a next injection site (e.g., the next injection site to be recommended to the user) based at least partially on the received injection site recommendation profile, as shown in act 418 of FIG. 4B. As noted above, FIG. 5 depicts a simplified process 500 for identifying a recommend injection site.

Referring to FIGS. 4A and 5 together, the generated injection site recommendation profile may include a logic flow including the selected injection sites, as discussed above in regard to act 402 of FIG. 4A. As a non-limiting example, the selected injection sites may include upper arm left, upper arm right, thigh left, thigh right, abdomen, buttocks right, and buttock left among other injection sites. Based on the selected injection cycle, the injection site determination system 104 may cycle through a list of the included injection sites. As noted above, the list may be ordered based on the selected injection cycle. For example, as depicted in FIG. 5, the injection site determination system 104 may start with a first injection site of the list of the included injection sites (e.g., the upper arm left), as show in box 502. The injection site determination system 104 may determine whether the first injection site has been previously used as an injection site during a current cycle (e.g., a current cycle through the list of included injection sites), as shown in act 504 of FIG. 5. If the injection site determination system 104 determines that the first injection site has not been previously used as an injection site during the current cycle, the injection site determination system 104 may identify the first injection site (e.g., the upper arm left) as the next injection site for the user (e.g., the next injection site to be recommended to the user), as shown in act 506 of FIG. 5.

If, alternatively, the injection site determination system 104 determines that the first injection site has been previously used as an injection site during the current cycle, the injection site determination system 104 may move down the list of the included injection sites to a second injection site (e.g., the upper arm right), as shown in box 508 of FIG. 5. The injection site determination system 104 may determine whether the second injection site has been previously used as an injection site during the current cycle, as shown in act 510 of FIG. 5. If the injection site determination system 104 determines that the second injection site has not been previously used as an injection site during the current cycle, the injection site determination system 104 may identify the second injection site (e.g., the upper arm right) as the next injection site, as shown in act 512 of FIG. 5.

If, alternatively, the injection site determination system 104 determines that the second injection site has been previously used as an injection site during the current cycle, the injection site determination system 104 may move down the list of the included injection sites to a third injection site (e.g., the upper arm right) and may repeat determining whether injection sites have been previously used as an injection site during the current cycle until the injection site determination system 104 identifies an injection site the has not been previously used as an injection site during the current cycle, as shown in act 511 of FIG. 5.

If the injection site determination system 104 does not identify an injection site the has not been previously used as an injection site during the current cycle, the injection site determination system 104 may continue through the list of the included injection sites until the injection site determination system 104 moves to a final injection site of the list of the included injection sites, as shown in box 513 of FIG. 5. The injection site determination system 104 may determine whether the final injection site has been previously used as an injection site during the current cycle, as shown in act 514 of FIG. 5. If the injection site determination system 104 determines that the final injection site has not been previously used as an injection site during the current cycle, the injection site determination system 104 may identify the final injection site (e.g., the upper arm right) as the next injection site, as shown in act 516 of FIG. 5.

If, alternatively, the injection site determination system 104 determines that the final injection site has been previously used as an injection site during the current cycle, the injection site determination system 104 may return to the first injection site and may commence a new cycle, as shown in act 518 of FIG. 5.

Referring again to FIG. 4B, upon identifying the next injection site, the injection site determination system 104 may optionally determine whether another factor may warrant recommending a different injection site than the identified next injection site, as shown in act 420 of FIG. 4B. For example, the injection site determination system 104 may determine whether another factor (e.g., glucose data or insulin dosing data) overrides the next injection site identified in act 418 of FIG. 4B.

In some embodiments, determining whether a different injection site is warranted includes determining whether received glucose data correlating to the identified next injection site warrants recommending a different injection site, as shown in act 422 of FIG. 4B. For example, in one or more embodiments, based on the received glucose data (as received in act 410 of FIG. 4A) correlating to the identified next injection site (e.g., glucose data related to an insulin injection previously given at the next injection site), the injection site determination system 104 may determine that the insulin was not properly absorbed at the next injection site and/or did not affect the user's glucose levels as anticipated. For instance, the injection site determination system 104 may determine that the identified next injection site has been overused such that the next injection site is not properly absorbing insulin. As used herein, the phrase "not properly absorbing insulin" may indicate that the received glucose data indicates that that a blood glucose level was not affected by an expected amount in response to previous injections within a given threshold. The threshold may be determined based on expert input data and/or relevant literature.

If the injection site determination system 104 determines that the identified next injection site is not properly absorbing insulin, the injection site determination system 104 may optionally identify a different injection site to recommend to the user, as shown in act 424 of FIG. 4B. In some embodiments, the injection site determination system 104 may identify the different injection site as a subsequent (e.g., a next) injection site within the selected cycle described above in regard to box 502 and FIG. 5. In other embodiments, the injection site determination system 104 may identify the different injection site as an injection site outside of the selected cycle. In further embodiments, the injection site determination system 104 may identify the different injection site as an injection site within the list showing a best insulin absorption based on the received glucose data. In additional embodiments, the injection site determination system 104 may identify the different injection site within a region of the user's body different from the region of the user's body including the identified next injection site. In other embodiments, the injection site determination system 104 may identify the different injection site within a same region of the user's body as the identified next injection site but within a different portion of the region. For example, the different injection site may be an upper left quadrant of the upper arm right and the identified injection site may include a lower right quadrant of the upper arm right. In some embodiments, identifying a different injection site may include adding specifics to the next injection site. For instance, identifying a different injection site may include adding details on where within a region of the user's body the injection should be made (e.g., making the injection within a particular portion of a region of the user's body (e.g., within an upper left quadrant of the upper arm right)).

In some embodiments, determining whether a different injection site is warranted includes determining whether received insulin dosing data correlating to the identified next injection site warrants recommending a different injection site, as shown in act 426. For example, in one or more embodiments, based at least partially on the received insulin dosing data (as received in act 412 of FIG. 4A) correlating to the identified next injection site, the injection site determination system 104 may determine that one or more of a type of the insulin to be administered or a size of the insulin dose is typically not injected in the recommended injection site. Typical injections sites based on types of insulin and/or sizes of insulin doses may be determined based on expert input data and/or clinical literature, which may be included within the external systems/resources 114. As a non-limiting example, the received insulin dosing data may indicate that the upcoming insulin dose is relatively large and is not typically injected in the identified next injection site (e.g., an upper arm). As another non-limiting example, the received insulin dosing data may indicate that the upcoming insulin dose is of a particular type (e.g., long acting (LA) insulin and rapid acting (RA) insulin) that is not typically injected in the identified next injection site (e.g., an upper arm).

If the injection site determination system 104 determines that the identified next injection site is not typically used for the size and/or type of the upcoming insulin dose, the injection site determination system 104 may optionally identify a different injection site than the identified next injection site, as shown in act 428 of FIG. 4B. For example, if the upcoming insulin dose is relatively large and the recommended site (e.g., upper arm) is not typically used for relatively large doses, the injection site determination system 104 may identify a different injection site that is more typically utilized for large doses.

Referring to acts 422-428 together, in some embodiments, identifying different injections sites (e.g., changing the injection site) may be stacked. For example, the injection site to recommended to a user may be changed to a different injection site based on one of the glucose data and the insulin dosing data, and then may be changed again based on the other of the glucose data and the insulin dosing data. In other embodiments, both the glucose data and the insulin dosing data may be considered at least substantially simultaneously such that the injection site to be recommended to the user is changed to align with both the glucose data and the insulin dosing data. In some embodiments, the injection site determination system 104 one or more algorithms to consider the selected cycle, glucose data, and/or insulin dosing data together in identifying the recommended injection site.

Referring still to acts 422-428 together, in some embodiments, whether or not the injection site determination system 104 changes the injection site to recommend to the user based on glucose data and/or insulin dosing data may be a selectable option when the user initiates creation of an injection site recommendation profile. In other words, whether or not the injection site determination system 104 is permitted to change the injection site to recommend to the user may be a selectable option when the user initiates creation of an injection site recommendation profile. Creating the injection site recommendation profile is further described below in regard to FIGS. 6A-6E.

Upon identifying a next injection site within a selected cycle and/or identifying a different injection site based at least partially on available data, the injection site determination system 104 may optionally provide a recommended injection site to the delivery device 118, as shown in act 430 of FIG. 4B. In some embodiments, the injection site determination system 104 may provide the next injection site or the different injection site as the recommended injection site determined according to acts 422-428 described above. For example, the injection site determination system 104 may wirelessly transmit the recommend injection site to the delivery device 118 via one or more of the network, Bluetooth, or any other wireless or wired method.

Responsive to receiving the recommended injection site, the delivery device 118 may display the recommend injection site on the display of the delivery device 118, as shown in act 432 of FIG. 4C. For example, when the delivery device 118 includes an insulin pen 200 as described above in regard to FIGS. 2A and 3, the insulin pen 200 may display the recommended injection site on the display screen 204 of the insulin pen 200. In additionally embodiments, when the delivery device 118 includes an insulin pen 200 and a dose-capture cap 202, the insulin pen 200 and/or a dose-capture cap 202 may display the recommended injection site on one or more of the display screen 204 of the insulin pen 200 or the display screen 210 of the dose-capture cap 202.

In some embodiments, upon identifying a recommended injection site and/or changing the recommended injection site, the injection site determination system 104 may optionally display the recommended injection site on a display of the client device 102, as shown in act 434 of FIG. 4C. For example, the injection site determination system 104 may display the recommended injection site within a graphical user interface of the application 112. Displaying the recommended injection site is described in further detail below in regard to FIGS. 6A-6X.

Referring still to FIG. 4C, the delivery device 118 may optionally detect an injection event, as shown in act 436 of FIG. 4C. In some embodiments, the delivery device 118 may detect an injection event subsequent to the recommended injection site being displayed on the delivery device 118 and/or client device 102. In one or more embodiments, the delivery device 118 may detect an injection event via any of the manners described above in regard to FIGS. 2 and 3. For instance, the delivery device 118 may detect an injection event by detecting the position of a plunger 318 of the delivery device 118.

Responsive to detecting an injection event, the injection site determination system 104 may optionally generate and cause the delivery device 118 and/or the client device 102 display a confirmation request, as shown in act 438 of FIG. 4C. For example, the delivery device 118 and/or the client device 102 may display a confirmation request asking the user to confirm that the user injected the insulin dose according to the recommended injection site. For example, when the delivery device 118 includes an insulin pen 200 and a dose-capture cap 202, the insulin pen 200 and/or a dose-capture cap 202 may display the confirmation request on one or more of the display screen 204 of the insulin pen 200 or the display screen 210 of the dose-capture cap 202. Additionally, the injection site determination system 104 may optionally display the confirmation request on a display of the client device 102.

Furthermore, the delivery device 118 and/or the client device 102 may detect a user interaction indicating whether or not the user injected the insulin at the recommended injection site, as shown in act 439 of FIG. 4C. For example, the delivery device 118 and/or the client device 102 may detect the user interaction via any of the input/output interfaces described above in regard to FIGS. 1-3 or any other suitable input interface.

Responsive to the delivery device 118 and/or the client device 102 detecting a user interaction indicating whether or not the user injected the insulin at the recommended injection site, the injection site determination system 104 may receive an indication of whether or not the user injected the insulin at the recommended injection site, as shown in act 440 of FIG. 4C.

Furthermore, the injection site determination system 104 may receive glucose data from the glucose monitor 116 subsequent to the injection event and based at least partially on the received indication may correlate the glucose data to the associated injection site, as shown in act 442 of FIG. 4C. As discussed above, the glucose data may be utilized to determine injection sites for future insulin doses.

Additionally, the injection site determination system 104 may repeat any of acts 416-442 of FIGS. 4A-4C for any number of insulin injections.

Referring to FIGS. 4A-4C together, in some embodiments, the injection site determination system 104 may add injection sites and/or regions of the user's body for injection sites based on the received glucose data and/or insulin dosing data, as is discussed in greater detail below in regard to FIG. 7.

In further embodiments, the injection site determination system 104 may determine a viable value (e.g., a wear and tear value) for each injection site utilized by the user based at least partially on the received glucose data and insulin dosing data associated with the injection site. In other words, injection site determination system 104 determine a severity of lipohypertrophy at given injection sites based at least partially on received glucose data and recommended injection sites. For example, a viable value may reflect a percentage of insulin that was absorbed relative to an amount of insulin that should have been absorbed at a healthy injection site. Likewise, the viable value may reflect an amount by which glucose in the user's blood was affected by an insulin dose relative to what the effect the insulin dose was expected to have on the user's blood. Furthermore, in some embodiments, injection cycles of injection site profiles may be determined based at least partially on the determined viable values of the injection sites. In some embodiments, the determined viable values may indicate how well the respective injection sites are absorbing insulin and/or how often the injection site should be utilized for a given future time period. In one or more embodiments, based at least partially on a determined viable value of a given injection site, the injection site determination system 104 may recommend an adjustment to an amount of an upcoming insulin dose. In yet further embodiments, based at least partially on determined viable values of injection sites within an injection site profile, the injection site determination system 104 may recommend adding injection sites to the injection site profile.

Referring to FIGS. 1-5 together, the injection site determination system 104 and methods described herein may encourage site rotation and may reduce the effects of lipohypertrophy caused by multiple daily injections. As a result, the injection site determination system and methods described herein may improve insulin delivery. Additionally, injection site determination system and methods may determine a severity of lipohypertrophy at given injection sites based at least partially on received glucose data and recommended injection sites.

FIGS. 6A-6E illustrate a flow of user interfaces including features of the environment 100 according to an embodiment. As will be described in more detail below, the components of the environment 100 as described in regard to FIGS. 1-5 may provide, alone and/or in combination with the other components, one or more graphical user interfaces ("GUIs"). A GUI typically includes one or more display regions and active/activatable regions. As used in this disclosure, a display region is a region of a GUI which displays information to a user. An activatable region is a region of a GUI, such as a button, slider, or a menu, which allows the user to take some action with respect to the GUI (e.g., if manipulated). Some display regions are also activatable regions in that the activatable regions display information and enable some action that may be taken by a user. In a contact-sensitive GUI, contacting a contact-sensitive area associated with an activatable region may activate that region (e.g., selecting a GUI button). Activatable regions may be displayed as GUI elements/objects, for example, buttons, sliders, selectable panes, menus, etc., all of various shapes and sizes. In particular, the components (e.g., the activatable regions of the GUI) may allow a user 110 to interact with a collection of display elements for a variety of purposes. In particular, FIGS. 4A-4L and the description that follows illustrate various example embodiments of the user interfaces and features that are in accordance with one or more embodiments.

Figure 6A:
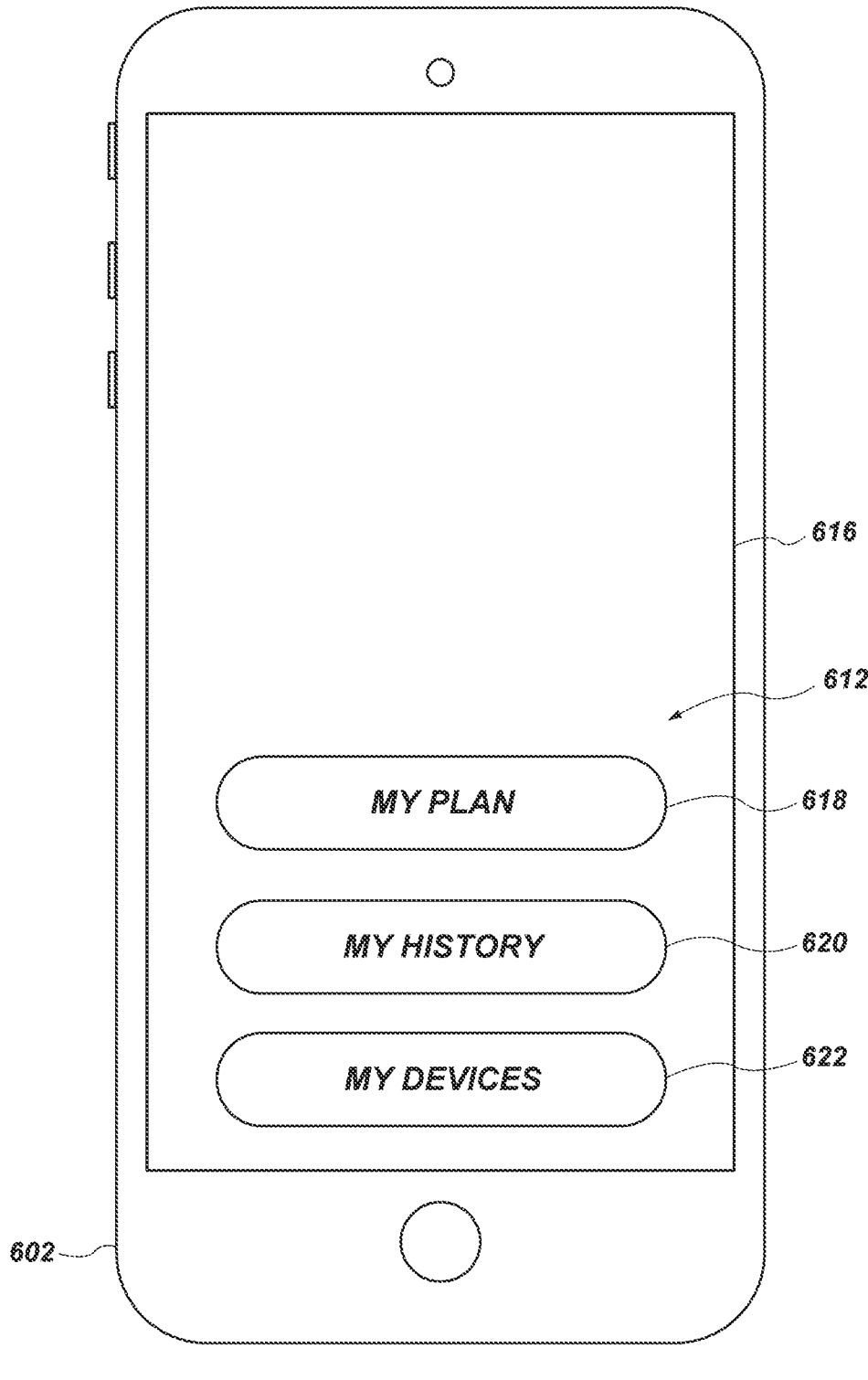

For example, FIG. 6A illustrates a client device 602 of an injection site determination system 104 user (e.g., the user 110 of FIG. 1) that may implement one or more of the components or features of the environment 100. As shown in FIG. 6A, in some embodiments, the client device 602 may include a tablet device. In some embodiments, the client device 602 is a handheld device, such as a mobile phone device (e.g., a smartphone). As used herein, the term "handheld device" refers to a device sized and configured to be held/operated in a single hand of the user 110 and/or worn and operated by one or more hands of the user 110. In additional or alternative examples, however, any other suitable computing device, such as, but not limited to, a larger wireless device, laptop or desktop computer, a personal digital assistant device, and/or any other suitable computing device may perform one or more of the processes and/or operations described herein.

The client device 602 includes a touch screen display 616 that may display user interfaces. Furthermore, the client device 602 receives and/or detects user input via the touch screen display 616. As used herein, a "touch screen display" refers to the display of a touch screen device. In one or more embodiments, a touch screen device may be the client device 602 with at least one surface upon which a user 110 may perform touch gestures (e.g., a laptop, a tablet computer, a personal digital assistant, a media player, a mobile phone, etc.). Additionally or alternatively, the client device 602 may include any other suitable input device, such as a touch pad or those described below with reference to FIG. 7.

Additionally, FIGS. 6A-6E show example GUIs of a tool application of an injection site determination system 104 for providing a variety of services including determining and recommending injection sites according to any of the manners described above. For instance, as shown in FIG. 6A, the touch screen display 616 of the client device 602 displays an initial GUI 612. The initial GUI 612 displays a plurality of selectable elements 618, 620, 622 including a selectable element 618 for accessing a user's plan for insulin therapy.

Figure 6B:
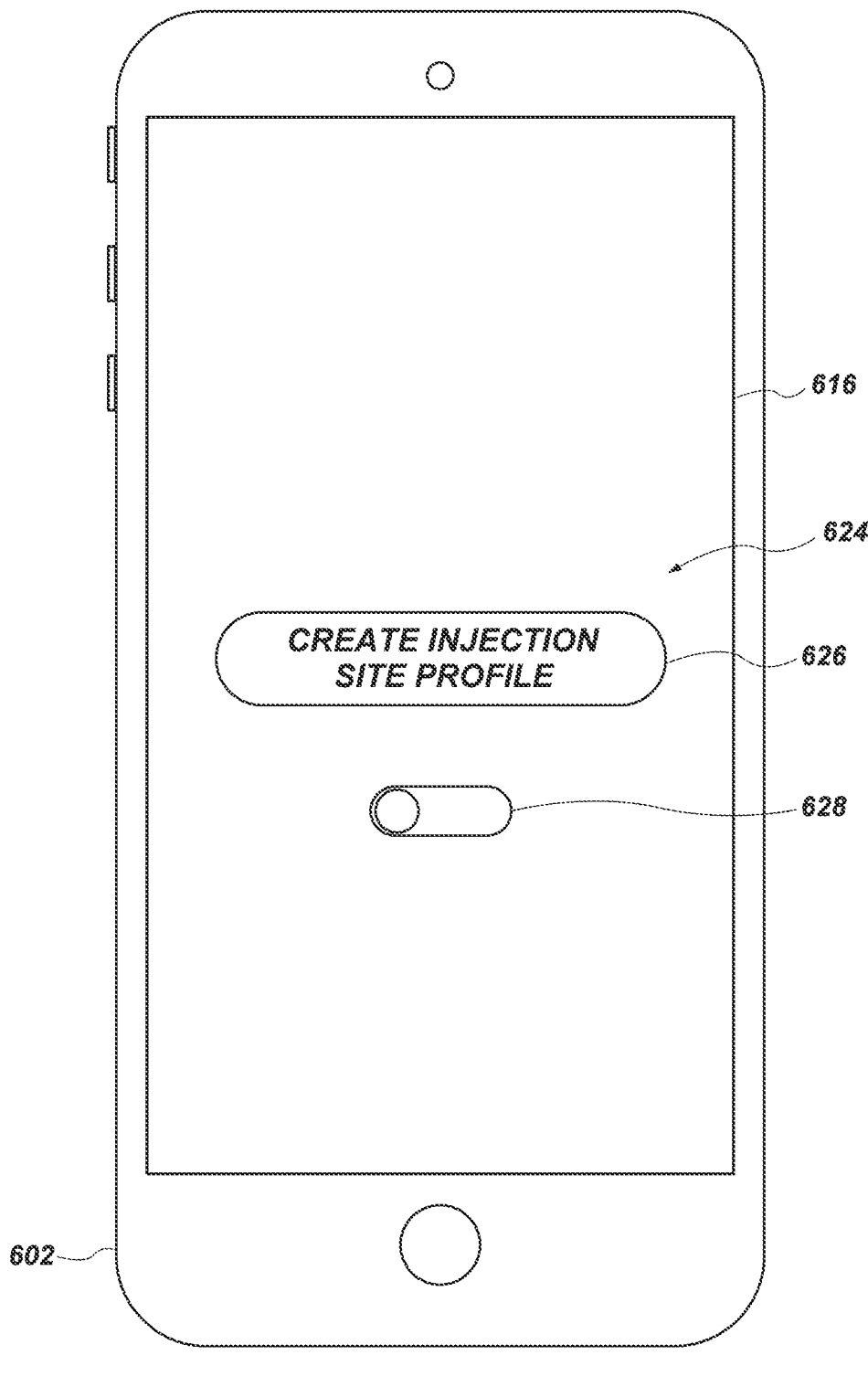

FIG. 6B shows an injection site profile creation GUI 624 for initiating creation of an injection site recommendation profile within the injection site determination system 104. The injection site profile creation GUI 624 may be displayed in response to a detected selection of the selectable element 618 of FIG. 6A. In some embodiments, the injection site profile creation GUI 624 may include a selectable element 626 to initiate creation of an injection site recommendation profile. Furthermore, the injection site profile creation GUI 624 may include a selectable element 628 to turn off or on injection site recommendation. For example, the selectable element 628 may include a toggle element.

Figure 6C:
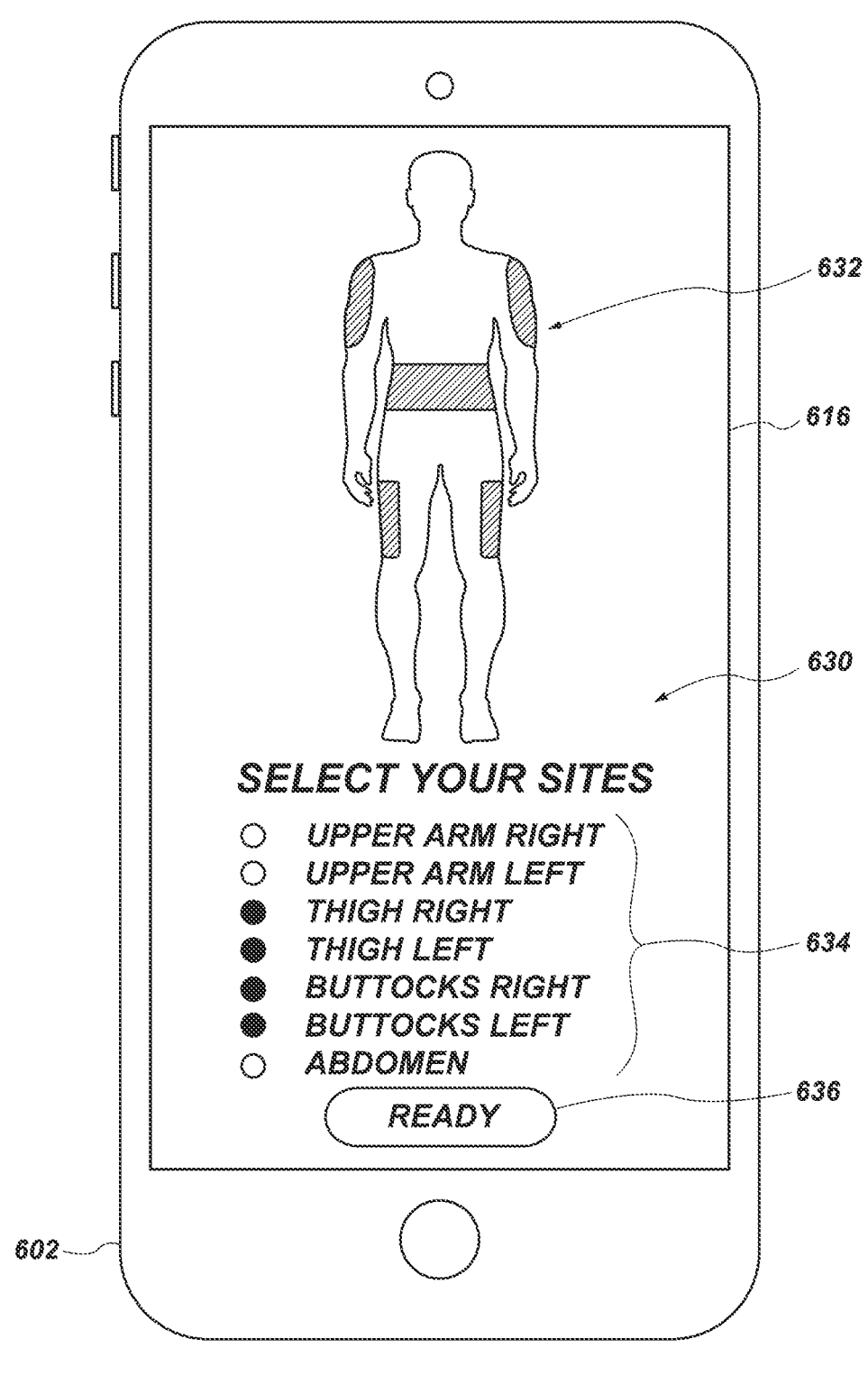

In response to a selection of the injection site profile creation GUI 624, the injection site determination system 104 may display a site selection GUI 630 for selecting injection sites to include within an injection site recommendation profile, as shown in FIG. 6C. For example, the site selection GUI 630 may facilitate the actions described above in regard to acts 404 and 406 of FIG. 4A. In some embodiments, the site selection GUI 630 may include a user body GUI 632 and a plurality of selectable elements 634 representing selectable injection sites. In one or more embodiments, the user body GUI 632 may include a schematic representation of the user body and may depict regions or areas of the body that the user may select. The injection sites may be selected via any of the actions described above in regard to acts 404 and 406 of FIG. 4A. The site selection GUI 630 may further include a selectable element 636 for indicating that the user has finished selecting injection sites.

Figure 6D:
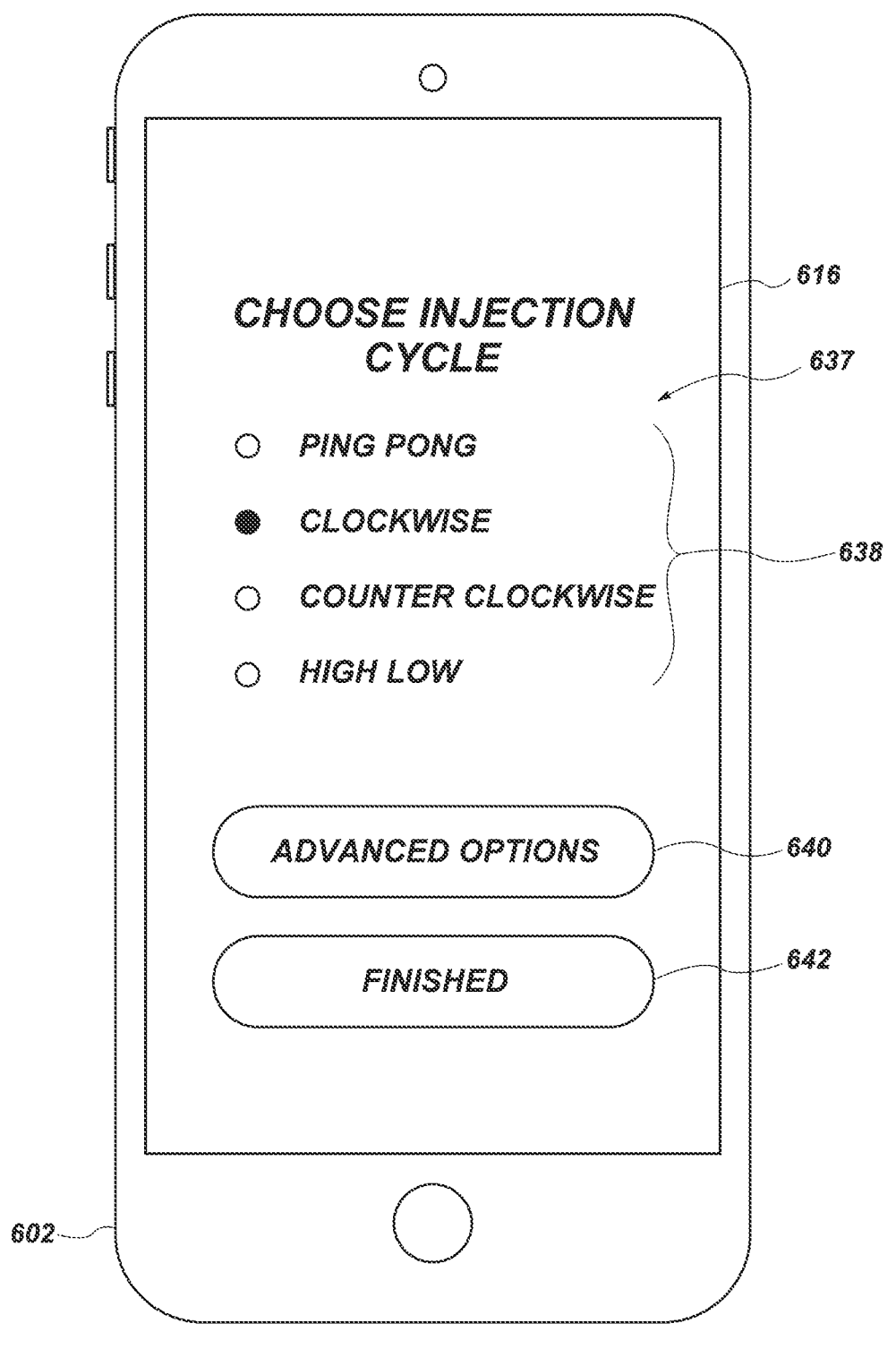

Responsive to a selection of the selectable element 636 indicating that the user has finished selecting injection sites, the injection site determination system 104 may display an injection cycle selection GUI 637 for selection an injection cycle to include within the injection site recommendation profile, as shown in FIG. 6D. For example, the injection cycle selection GUI 637 may facilitate the actions described above in regard to acts 408 and 409 of FIG. 4A. In some embodiments, the site selection GUI 630 may include a plurality of selectable elements 638 representing injection cycles and a selectable element 640 of additional options regarding recommending injection sites. The site selection GUI 630 may further include a selectable element 642 for indicating that the user has finished selecting an injection cycle. In response to a detected selection of the selectable element 642, the injection site determination system 104 may generate the injection site recommendation profile according to any of the action described above in regard to act 410 of FIG. 4A.

Figure 6E:
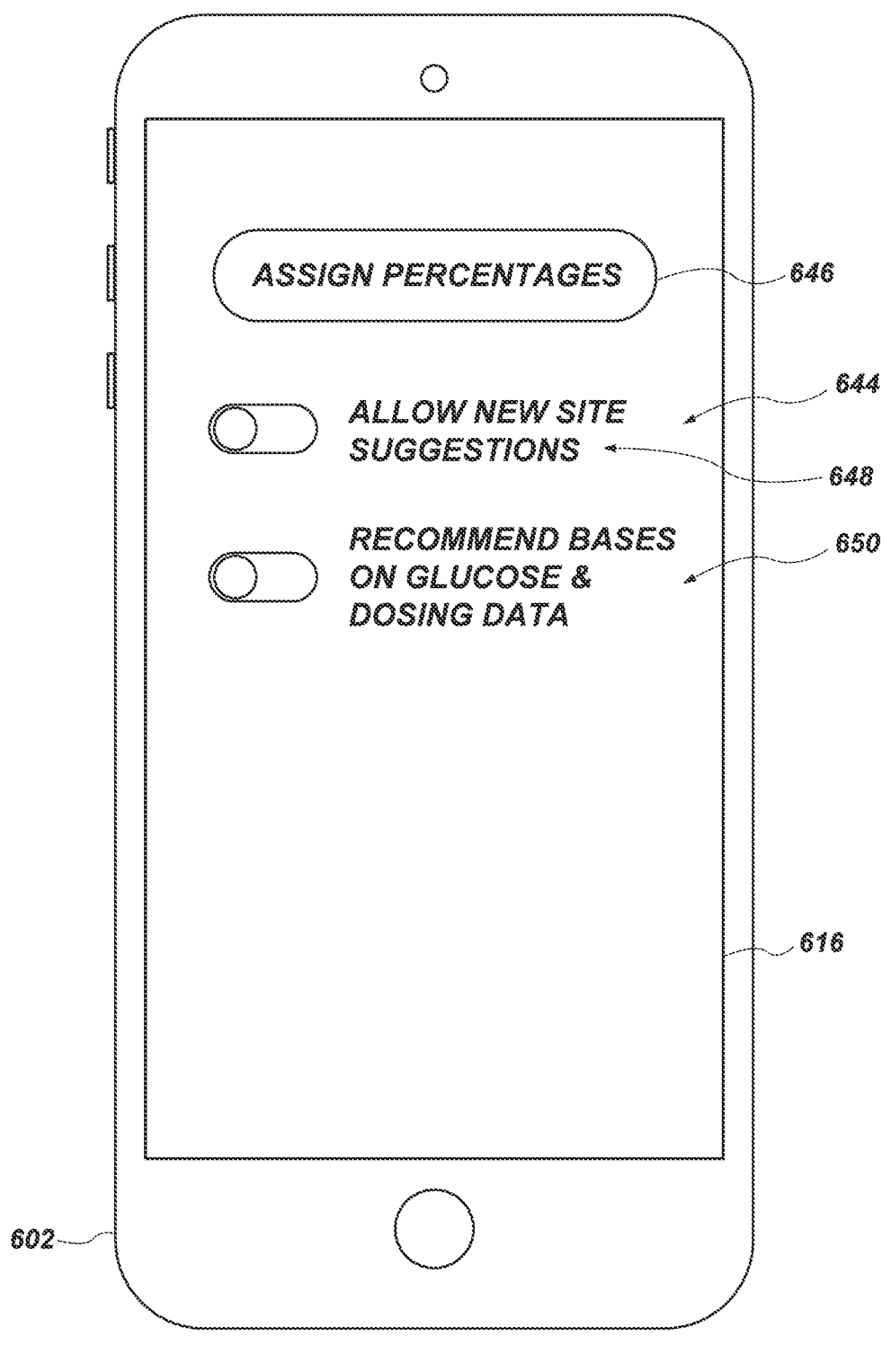

In response to selection of selectable element 640, the injection site determination system 104 may display an advanced options GUI 644, as shown in FIG. 6E. In some embodiments, the advanced options GUI 644 may include a selectable element 646 enabling the user to assign user-selected percentages to injection sites such that the injection sites are selected and recommended according to the user-selected percentages. For example, if a given injection site is given a user-selected 33%, the given injection site may be selected and recommended 33% of the time. Additionally, the advanced options GUI 644 may include a selectable element 648 enabling the user to allow new injection site suggestions (e.g., new injection sites beyond what was previously selected by the user in acts 404 and 406 of FIG. 4A). In some embodiments, the selectable element 648 is a toggle element. Furthermore, the advanced options GUI 644 may include a selectable element 650 for enabling the user to allow the injection site determination system 104 to recommend injection sites based at least partially on glucose data and insulin dosing data. For instance, the selectable element 650 may allow the injection site determination system 104 to recommend injection sites according to any of the actions described above in regard to acts 420-428 of FIG. 4B.

FIG. 7 depicts a flow chart of a method 700 of determining additional and/or new injection sites for a user according to one or more embodiments. In one or more embodiments, the method 700 may include the injection site determination system 104 providing a recommended injection site to a user, as shown in act 702 of FIG. 7. For example, providing the recommended injection site to the user may include any of the actions described above in regard to acts 402-430 of FIGS. 4A and 4B.

Responsive to providing the recommended injection site to a user, the method 700 may include receiving a confirmation of an injection, as shown in act 704 of FIG. 7. For example, the injection site determination system 104 may determine whether or not the user made an injection according to the recommended injection site (e.g., made an injection at the recommended injection site). For instance, receiving a confirmation of an injection may include any of the actions described above in regard to acts 438-440 of FIG. 4C.

Additionally, the method 700 may optionally include receiving glucose data, as shown in act 706 of FIG. 7. In some embodiments, the injection site determination system 104 may receive glucose data from a glucose monitor. In one or more embodiments, the injection site determination system 104 may receive the glucose data subsequent to an injection at the recommended injection site. As a non-limiting example, receiving the glucose data may include any of the actions described above in regard to act 411 of FIG. 4A.

Furthermore, the method 700 may optionally include receiving insulin dosing data, as shown in act 708 of FIG. 7. In some embodiments, the injection site determination system 104 may receive insulin dosing data from one or more of the delivery device 118, the application 112, and/or the external systems/resources 114. In some embodiments, the insulin dosing data may include an insulin dosing type (e.g., long acting (LA) insulin and rapid acting (RA) insulin), a brand of insulin, a dosing timing, an insulin dosing size, etc.

For example, receiving insulin dosing data may include any of the action described above in regard to act 412 of FIG. 4A.

In some embodiments, the method 700 may include applying one or more machine-learning models to a combination of one or more of injection site data, the received glucose data, or the received insulin dosing data, as shown in act 710 of FIG. 7. In one or more embodiments, the injection site determination system 104 may apply the machine-learning models to a combination of one or more of injection site data, the received glucose data, or the received insulin dosing data to determine injection sites to recommend to the user. For example, the injection site determination system 104 may apply the machine-learning models to a combination of one or more of injection site data, the received glucose data, or the received insulin dosing data to determine additional injection sites to recommend to the user, as shown in act 712 of FIG. 7.

In one or more embodiments, applying the one or more machine-learning models may include analyzing the a combination of one or more of injection site data, the received glucose data, or the received dosing data may include machine learning and/or deep learning techniques that include providing training corpora to a matching learning algorithm or neural network to train a machine to determine additional injection sites for the user. In some embodiments, the injection site determination system 104 may analyze the combination of one or more of injection site data, the received glucose data, or the received insulin dosing data utilizing one or more of regression models (e.g., a set of statistical processes for estimating the relationships among variables), classification models, and/or phenomena models. Additionally, the machine-learning models may include a quadratic regression analysis, a logistic regression analysis, a support vector machine, a Gaussian process regression, ensemble models, or any other regression analysis. Furthermore, in yet further embodiments, the machine-learning models may include decision tree learning, regression trees, boosted trees, gradient boosted tree, multilayer perceptron, one-vs-rest, Naïve Bayes, k-nearest neighbor, association rule learning, a neural network, deep learning, pattern recognition, or any other type of machine-learning.

For example, the injection site determination system 104 may apply one or more of the above described machine learning techniques to the combination of one or more of injection site data, the received glucose data, or the received insulin dosing data in conjunction with any subsequent data or data from the external systems/resources 114. Furthermore, by applying the one or more machine-learning techniques to the above-described data, the injection site determination system 104 may determine injection sites to recommend to the user. In some embodiments, an operation flow and/or logic of the injection site determination system 104 may include flows of actions that are utilized in different scenarios. For instance, a first operation flow may include a decision tree utilized when insulin is not properly absorbed at a given injection site. Another operation flow may include a decision tree utilized when a user refuses to inject at a recommended injection site. In view of the foregoing, the operation flows may be related to feedback data received from the user, a delivery device 118, the glucose monitor 116, and/or external systems/resources 114

As a non-limiting example, the injection site determination system 104 may utilize the feedback loop of the injection site determination system 104 providing recommended injection sites and receiving confirmation data from the user and/or glucose data and insulin dosing data. In other words, via the machine-learning model techniques, the injection site determination system 104 may learn correlations between recommended injection sites and confirmation data, glucose data, and/or insulin dosing data. Put another way, the injection site determination system 104 may learn the relationship between the recommended injection sites and the operation flows and/or the logic flows of the injection site determination system 104. For example, the machine-learning models are trained via supervised and/or unsupervised learning, as is known in the art. After a sufficient number of iterations, the machine-learning models become trained machine-learning models. In some embodiments, the machine-learning models may also be trained on historical data (e.g., glucose data, insulin dosing data, injection site data, etc.) from previous injections and/or expert input data and/or relevant literature.

In some embodiments, determining additional injection sites to recommend to the user may include dividing regions of the user's body into additional injection sites, as shown in act 714 of FIG. 7. For example, the injection site determination system 104 may determine to divide a region (e.g., an upper arm right region) into a plurality of injection site in comparison to the single injection site. For instance, based on glucose data received regarding a injection site at a given region, the injection site determination system 104 may determine to improve absorption, the region should be divided into multiple injection sites.

In one or more embodiments, determining additional injection sites to recommend to the user may include adding regions of the user's body for additional injection sites, as shown in act 716 of FIG. 7. For example, the injection site determination system 104 may determine to add or recommend adding one or more regions and/or one or more injection sites to a selected injection cycle. For instance, based on glucose data received regarding injection sites of a selected injection cycle and/or insulin dosing data, the injection site determination system 104 may determine (e.g., learn) to recommend adding regions and/or injection sites to a selection injection cycle to improve insulin therapy of the user (e.g., improve absorption, reduce pain, etc.).

FIG. 8 is a block diagram of an exemplary computing device 800 that may be utilized as a client device (e.g., client device 102) and/or an injection site determination system (e.g., injection site determination system 104) that may be configured to perform one or more of the processes described above. One will appreciate that one or more computing devices may implement the computing device 800. The computing device 800 may comprise a processor 802, a memory 804, a storage device 806, an I/O interface 808, and a communication interface 810, which may be communicatively coupled by way of a communication infrastructure 812. While an exemplary computing device is shown in FIG. 8, the components illustrated in FIG. 8 are not intended to be limiting. Additional or alternative components may be used in other embodiments. Furthermore, in certain embodiments, the computing device 800 may include fewer components than those shown in FIG. 8. Components of the computing device 800 shown in FIG. 8 will now be described in additional detail.

In one or more embodiments, the processor 802 includes hardware for executing instructions, such as those making up a computer program. As an example and not by way of limitation, to execute instructions, the processor 802 may retrieve (or fetch) the instructions from an internal register, an internal cache, the memory 804, or the storage device 806 and decode and execute them. In one or more embodiments, the processor 802 may include one or more internal caches for data, instructions, or addresses. As an example and not by way of limitation, the processor 802 may include one or more instruction caches, one or more data caches, and one or more translation lookaside buffers (TLBs). Instructions in the instruction caches may be copies of instructions in the memory 804 or the storage device 806.

The memory 804 may be used for storing data, metadata, and programs for execution by the processor(s). The memory 804 may include one or more of volatile and non-volatile memories, such as Random Access Memory ("RAM"), Read-Only Memory ("ROM"), a solid state disk ("SSD"), Flash memory, Phase Change Memory ("PCM"), or other types of data storage. The memory 804 may be internal or distributed memory.

The storage device 806 includes storage for storing data or instructions. As an example and not by way of limitation, storage device 806 may comprise a non-transitory storage medium described above. The storage device 806 may include a hard disk drive (HDD), a floppy disk drive, flash memory, an optical disc, a magneto-optical disc, magnetic tape, or a Universal Serial Bus (USB) drive or a combination of two or more of these. The storage device 806 may include removable or non-removable (or fixed) media, where appropriate. The storage device 806 may be internal or external to the computing device 800. In one or more embodiments, the storage device 806 is non-volatile, solid-state memory. In other embodiments, the storage device 806 includes read-only memory (ROM). Where appropriate, this ROM may be mask programmed ROM, programmable ROM (PROM), erasable PROM (EPROM), electrically erasable PROM (EEPROM), electrically alterable ROM (EAROM), or flash memory or a combination of two or more of these.

The I/O interface 808 allows a user to provide input to, receive output from, and otherwise transfer data to and receive data from computing device 800. The I/O interface 808 may include a mouse, a keypad or a keyboard, a touch screen, a camera, an optical scanner, network interface, modem, other known I/O devices or a combination of such I/O interfaces. The I/O interface 808 may include one or more devices for presenting output to a user, including, but not limited to, a graphics engine, a display (e.g., a display screen), one or more output drivers (e.g., display drivers), one or more audio speakers, and one or more audio drivers. In certain embodiments, the I/O interface 808 is configured to provide graphical data to a display for presentation to a user. The graphical data may be representative of one or more graphical user interfaces and/or any other graphical content as may serve a particular implementation.

The communication interface 810 may include hardware, software, or both. In any event, the communication interface 810 may provide one or more interfaces for communication (such as, for example, packet-based communication) between the computing device 800 and one or more other computing devices or networks. As an example and not by way of limitation, the communication interface 810 may include a network interface controller (NIC) or network adapter for communicating with an Ethernet or other wire-based network or a wireless NIC (WNIC) or wireless adapter for communicating with a wireless network, such as a WI-FI.

Additionally or alternatively, the communication interface 810 may facilitate communications with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, the communication interface 810 may facilitate communications with a wireless PAN (WPAN) (such as, for example, a BLUETOOTH®WPAN), a WI-FI network, a WI-MAX network, a cellular telephone network (such as, for example, a Global System for Mobile Communications (GSM) network), or other suitable wireless network or a combination thereof.

Additionally, the communication interface 810 may facilitate communications various communication protocols. Examples of communication protocols that may be used include, but are not limited to, data transmission media, communications devices, Transmission Control Protocol ("TCP"), Internet Protocol ("IP"), File Transfer Protocol ("FTP"), Telnet, Hypertext Transfer Protocol ("HTTP"), Hypertext Transfer Protocol Secure ("HTTPS"), Session Initiation Protocol ("SIP"), Simple Object Access Protocol ("SOAP"), Extensible Mark-up Language ("XML") and variations thereof, Simple Mail Transfer Protocol ("SMTP"), Real-Time Transport Protocol ("RTP"), User Datagram Protocol ("UDP"), Global System for Mobile Communications ("GSM") technologies, Code Division Multiple Access ("CDMA") technologies, Time Division Multiple Access ("TDMA") technologies, Short Message Service ("SMS"), Multimedia Message Service ("MMS"), radio frequency ("RF") signaling technologies, Long Term Evolution ("LTE") technologies, wireless communication technologies, in-band and out-of-band signaling technologies, and other suitable communications networks and technologies.

The communication infrastructure 812 may include hardware, software, or both that couples components of the computing device 800 to each other. As an example and not by way of limitation, the communication infrastructure 812 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination thereof.

The embodiments of the disclosure described above and illustrated in the accompanying drawing figures do not limit the scope of the invention, since these embodiments are merely examples of embodiments of the invention, which is defined by the appended claims and their legal equivalents. Any equivalent embodiments are intended to be within the scope of this invention. Indeed, various modifications of the present disclosure, in addition to those shown and described herein, such as alternative useful combinations of the content features described, may become apparent to those skilled in the art from the description. Such modifications and embodiments are also intended to fall within the scope of the appended claims and legal equivalents.

What is claimed is:

1. A method of improving insulin delivery via subcutaneous injections, comprising:

an injection site profile creation graphical user interface (GUI) displaying on a client device:

a user selectable injection site profile creation element that when selected by a particular user initiates creation of an injection site recommendation profile, wherein the injection site recommendation profile is generated for a particular user and includes a selected injection site cycle and a plurality of selected injection sites for upcoming injection events, and wherein the selected injection site cycle is an order for cycling through the plurality of injection sites and is selected by the particular user, and a user selectable injection site recommendation toggle element device that when selected turns on or off an injection site recommendation;

upon selection of the user selectable injection site profile creation element, an injection site selection GUI displaying on the client device:

a user body depicting regions or areas of the user body that may be selected as part of the injection site recommendation profile, a plurality of user selectable injection site elements each representing a different injection site for the injection site recommendation profile, and a user selectable injection site completion element that when selected by the particular user causes an injection cycle selection GUI to be displayed on the client device, wherein, upon selection of any of the plurality of user selectable injection site elements, the injection site selection GUI displaying a selection indicator next to the selected to the particular user selectable injection site element;

upon selection of the user selectable injection site completion element, the injection cycle selection GUI displaying on the client device;

a plurality of user selectable injection cycle option elements each representing a different type of injection cycle, and a user selectable injection cycle completion element that when selected by the particular user instructs the injection site determination system to generate the injection site recommendation profile;

the injection site determination system receiving, via the injection site selection GUI, a selection of a plurality of injection site inputs directed to a plurality of selected injection sites to include within the injection site recommendation profile;

the injection site determination system receiving, via the injection cycle selection GUI, a selection of the selected injection cycle to utilize within the injection site recommendation profile;

generating the injection site recommendation profile for the particular user based on the received selection of the plurality of injection site inputs and the received selection of the selected injection cycle;

the injection site determination system receiving from a delivery device via a network an indication of an injection event of an upcoming insulin dose;

the injection site determination system determining that a previous injection event of a previous insulin dose was administered at a first injection site;

based on the first injection site of the previous injection event, the injection site determination system identifying a next injection site to recommend for the upcoming insulin dose according to a selected injection site cycle of an injection site recommendation profile, wherein the injection site recommendation profile is generated for a particular user and includes the selected injection site cycle and a plurality of injection sites for upcoming injection events, and wherein the selected injection site cycle is an order for cycling through the plurality of injection sites and is selected by the particular user; and transmitting via the network a recommended injection site to a delivery device to be displayed on the delivery device.

2. The method of claim 1, further comprising receiving a second indication that an injection was administered according to the recommended injection site.

3. The method of claim 1, further comprising:

determining that one or more factors warrants selecting an injection site other than the identified next injection site as the recommended injection site; and based on the one or more factors, selecting a different injection site different from the identified next injection site as the recommended injection site.

4. The method of claim 3, wherein determining that one or more factors warrant selecting an injection site other than the identified next injection site as the recommended injection site comprises:

receiving glucose data related to one or more injection sites of the injection site recommendation profile; and determining that the glucose data indicates that insulin was not properly absorbed at the identified next injection site during a previous injection.

5. The method of claim 3, wherein determining that one or more factors warrants selecting an injection site other than the identified next injection site as the recommended injection site comprises:

receiving insulin dosing data related to the upcoming insulin dose; and determining that the insulin dosing data indicates that the upcoming insulin dose is a size or type that is typically not administered at the identified next injection site.

6. The method of claim 1, wherein transmitting a recommended injection site to a delivery device to be displayed on the delivery device comprising transmitting the recommended injection to an insulin delivery pen to be displayed on the insulin delivery pen.

7. The method of claim 1, further comprising:

generating a confirmation request asking whether insulin was administered at the recommended injection site; and transmitting the confirmation request to the delivery device.

8. The method of claim 1, wherein the selected injection site cycle comprises one of a clockwise cycle, a counter-clockwise cycle, a ping pong cycle, a random cycle, or a high-low cycle.

9. The method of claim 1, wherein detecting the injection event of the upcoming insulin dose includes receiving an indication of an uncapping event; and responsive to the uncapping event, identifying the next injection site to recommend for the upcoming insulin dose.

10. A system for improving insulin delivery, the system comprising:

at least one processor; and at least one non-transitory computer-readable storage medium storing instructions thereon that, when executed by the at least one processor, cause the system to:

instruct an injection site profile creation graphical user interface (GUI) to display on a client device:

a user selectable injection site profile creation element that when selected by a particular user initiates creation of an injection site recommendation profile, wherein the injection site recommendation profile is generated for a particular user and includes a selected injection site cycle and a plurality of selected injection sites for upcoming injection events, and wherein the selected injection site cycle is an order for cycling through the plurality of injection sites and is selected by the particular user, and a user selectable injection site recommendation toggle element device that when selected turns on or off an injection site recommendation;

upon selection of the user selectable injection site profile creation element, instruct an injection site selection GUI to display on the client device:

a user body depicting regions or areas of the user body that may be selected as part of the injection site recommendation profile, a plurality of user selectable injection site elements each representing a different injection site for the injection site recommendation profile, and a user selectable injection site completion element that when selected by the particular user causes an injection cycle selection GUI to be displayed on the client device, wherein, upon selection of any of the plurality of user selectable injection site elements, the injection site selection GUI is instructed to display a selection indicator next to the selected to the particular user selectable injection site element;

upon selection of the user selectable injection site completion element, instruct the injection cycle selection GUI to display on the client device:

a plurality of user selectable injection cycle option elements each representing a different type of injection cycle, and a user selectable injection cycle completion element that when selected by the particular user instructs the system to generate the injection site recommendation profile;

receive a selection of a plurality of injection site inputs directed to the plurality of injection sites to include within the injection site recommendation profile;

receive a selection of the injection cycle to utilize within the injection site recommendation profile;

generate the injection site recommendation profile for the particular user;

receive from a delivery device via a network an indication of an injection event of an upcoming insulin dose;

determine that a previous injection event of a previous insulin dose was administered at a first injection site;

based on the first injection site of the previous injection event, identify a next injection site to recommend for the upcoming insulin dose according to a selected injection site cycle of an injection site recommendation profile, wherein the injection site recommendation profile is generated for a particular user and includes the selected injection site cycle and a plurality of injection sites for upcoming injection events, and wherein the selected injection site cycle is an order for cycling through the plurality of injection sites and is selected by the particular user; and transmit, via a network, a recommended injection site to a delivery device to be displayed on the delivery device.

11. The system of claim 10, wherein the selected injection site cycle comprises one of a clockwise cycle, a counterclockwise cycle, a ping pong cycle, a random cycle, or a high-low cycle.

12. The system of claim 10, further comprising instructions that, when executed by the at least one processor, cause the system to:

detect the injection event of the upcoming insulin dose upon receipt of an indication of an uncapping event; and responsive to the uncapping event, identify the next injection site to recommend for the upcoming insulin dose.

13. The system of claim 10, further comprising instructions that, when executed by the at least one processor, cause the system to receive a second indication that an injection was administered according to the recommended injection site.

14. The system of claim 10, wherein identifying a next injection site to recommend for the upcoming insulin dose comprises identifying the next injection site based at least partially via one or more machine learning models.

15. The system of claim 10, further comprising instructions that, when executed by the at least one processor, cause the system to:

determine that one or more factors warrants selecting an injection site other than the identified next injection site as the recommended injection site; and based on the one or more factors, select a different injection site different from the identified next injection site as the recommended injection site.

16. The system of claim 15, wherein the system determines that one or more factors warrant selecting an injection site other than the identified next injection site as the recommended injection site upon:

receiving glucose data related to one or more injection sites of the injection site recommendation profile; and determining that the glucose data indicates that insulin was not properly absorbed at the identified next injection site during a previous injection.

17. The system of claim 15, wherein the system determines that one or more factors warrants selecting an injection site other than the identified next injection site as the recommended injection site upon:

receiving insulin dosing data related to the upcoming insulin dose; and determining that the insulin dosing data indicates that the upcoming insulin dose is a size or type that is typically not administered at the identified next injection site.

18. A non-transitory computer-readable medium storing instructions thereon that, when executed by at least one processor, cause the at least one processor to perform steps comprising:

an injection site profile creation graphical user interface (GUI) displaying on a client device:

a user selectable injection site profile creation element that when selected by a particular user initiates creation of an injection site recommendation profile, wherein the injection site recommendation profile is generated for a particular user and includes a selected injection site cycle and a plurality of selected injection sites for upcoming injection events, and wherein the selected injection site cycle is an order for cycling through the plurality of injection sites and is selected by the particular user, and a user selectable injection site recommendation toggle element device that when selected turns on or off an injection site recommendation;

upon selection of the user selectable injection site profile creation element, an injection site selection GUI displaying on the client device:

a user body depicting regions or areas of the user body that may be selected as part of the injection site recommendation profile, a plurality of user selectable injection site elements each representing a different injection site for the injection site recommendation profile, and a user selectable injection site completion element that when selected by the particular user causes an injection cycle selection GUI to be displayed on the client device, wherein, upon selection of any of the plurality of user selectable injection site elements, the injection site selection GUI displaying a selection indicator next to the selected to the particular user selectable injection site element;

upon selection of the user selectable injection site completion element, the injection cycle selection GUI displaying on the client device:

a plurality of user selectable injection cycle option elements each representing a different type of injection cycle, and a user selectable injection cycle completion element that when selected by the particular user instructs an injection site determination system to generate the injection site recommendation profile;

the injection site determination system receiving, via the injection site selection GUI, a selection of a plurality of injection site inputs directed to a plurality of selected injection sites to include within the injection site recommendation profile;

the injection site determination system receiving, via the injection cycle selection GUI, a selection of the selected injection cycle to utilize within the injection site recommendation profile;

generating the injection site recommendation profile for the particular user based on the received selection of the plurality of injection site inputs and the received selection of the selected injection cycle;

generating an injection site recommendation profile for a particular user based at least partially on a plurality of selected injection sites selected by the particular user and a selected injection site cycle, wherein the selected injection site cycle is an order for cycling through the plurality of selected injection sites selected by the particular user;

the injection site determination system receiving from a delivery device via a network an indication of an upcoming insulin dose;

the injection site determination system determining that a previous injection event of a previous insulin dose was administered at a first injection site;

based on the first injection site of the previous injection event, the injection site determination system identifying a next injection site to recommend for the upcoming insulin dose according to the selected injection site cycle; and transmitting, via a network, a recommended injection site to a delivery device to be displayed on the delivery device.

* * * * *